US011922656B2

(12) United States Patent
Maurer et al.

(10) Patent No.: US 11,922,656 B2
(45) Date of Patent: Mar. 5, 2024

(54) PARTIAL DEFORMATION MAPS FOR RECONSTRUCTING MOTION-AFFECTED TREATMENT DOSE USING MACHINE LEARNING

(71) Applicant: Accuray Incorporated, Sunnyvale, CA (US)

(72) Inventors: Calvin R. Maurer, San Jose, CA (US); Eric Schnarr, McFarland, WI (US); Rich Holloway, Chapel Hill, NC (US); Jacob Shea, Cross Plains, WI (US); Charles Brandon Frederick, Raleigh, NC (US); Kevin Gorczowski, Chapel Hill, NC (US); Robert Elijah Broadhurst, Carrboro, NC (US); Mark Foskey, Chapel Hill, NC (US)

(73) Assignee: Accuray Incorporated, Sunnyvale, CA (US)

( * ) Notice: Subject to any disclaimer, the term of this patent is extended or adjusted under 35 U.S.C. 154(b) by 694 days.

(21) Appl. No.: 17/098,215

(22) Filed: Nov. 13, 2020

(65) Prior Publication Data
US 2021/0154496 A1 May 27, 2021

Related U.S. Application Data

(60) Provisional application No. 62/940,037, filed on Nov. 25, 2019.

(51) Int. Cl.
*G06N 3/088* (2023.01)
*A61N 5/10* (2006.01)
(Continued)

(52) U.S. Cl.
CPC ............... *G06T 7/74* (2017.01); *A61N 5/103* (2013.01); *A61N 5/1031* (2013.01);
(Continued)

(58) Field of Classification Search
CPC ..... G06T 7/74; G06T 7/246; G06T 7/344; G06T 7/75; G06T 7/0012; G06T 2200/04;
(Continued)

(56) References Cited

U.S. PATENT DOCUMENTS 10,810,460 B2 * 10/2020 Ngo Dinh ............... G16H 50/20
2019/0333623 A1 * 10/2019 Hibbard ............... A61N 5/1039

FOREIGN PATENT DOCUMENTS

EP 3501603 A1 6/2019
EP 3501604 A1 6/2019
(Continued)

OTHER PUBLICATIONS

International Search Report by International Searching Authority for PCT/US2020/061112 dated Feb. 16, 2021.

*Primary Examiner* — David P Porta
*Assistant Examiner* — Fani Polyzos Boosalis
(74) *Attorney, Agent, or Firm* — Womble Bond Dickinson (US) LLP

(57) ABSTRACT

A method comprises inputting a treatment planning image of a target subject into a machine learning system. The method further comprises determining, by the machine learning system, a first target-subject-specific model of the treatment planning image. The method further comprises applying, by a processing device, the first target-subject-specific model to the treatment planning image to generate a transformed treatment planning image corresponding to a first position of a plurality of positions of the target subject. The method further comprises comparing the transformed treatment planning image to a reference image. The method further comprises, based on the comparing, modifying one or more parameters of the first target-subject-specific model to generate a second target-subject-specific model corresponding to a second position of the plurality of positions. The method further comprises controlling a treatment device based on (Continued)

the second target-subject-specific model to deliver a treatment to the target subject.

51 Claims, 14 Drawing Sheets

(51) Int. Cl.
| | |
|---|---|
| *G06N 3/045* | (2023.01) |
| *G06N 3/08* | (2023.01) |
| *G06N 20/00* | (2019.01) |
| *G06T 7/00* | (2017.01) |
| *G06T 7/246* | (2017.01) |
| *G06T 7/33* | (2017.01) |
| *G06T 7/73* | (2017.01) |
| *G06N 3/047* | (2023.01) |
| *G06N 5/01* | (2023.01) |

(52) U.S. Cl.
CPC ......... *A61N 5/1037* (2013.01); *A61N 5/1039* (2013.01); *A61N 5/1049* (2013.01); *A61N 5/1082* (2013.01); *G06N 3/045* (2023.01); *G06N 3/08* (2013.01); *G06N 3/088* (2013.01); *G06N 20/00* (2019.01); *G06T 7/0012* (2013.01); *G06T 7/246* (2017.01); *G06T 7/344* (2017.01); *G06T 7/75* (2017.01); *A61N 2005/1051* (2013.01); *A61N 5/1083* (2013.01); *G06N 3/047* (2023.01); *G06N 5/01* (2023.01); *G06T 2200/04* (2013.01); *G06T 2207/10076* (2013.01); *G06T 2207/10081* (2013.01); *G06T 2207/10116* (2013.01); *G06T 2207/10124* (2013.01); *G06T 2207/20081* (2013.01); *G06T 2207/20084* (2013.01); *G06T 2207/30096* (2013.01)

(58) Field of Classification Search
CPC . G06T 2207/10076; G06T 2207/10124; G06T 2207/20081; G06T 2207/20084; G06T 2207/30096; G06N 20/00; G06N 3/045; G06N 3/08; G06N 3/088; G06N 3/047; G06N 5/01; A61N 5/103; A61N 5/1031; A61N 5/1037; A61N 5/1039; A61N 5/1049; A61N 5/1082; A61N 5/1083; A61N 2005/1051
See application file for complete search history.

(56) References Cited

FOREIGN PATENT DOCUMENTS

| | | |
|---|---|---|
| KR | 102131742 B1 | 7/2020 |
| WO | 2009054879 A1 | 4/2009 |
| WO | 2018048575 A1 | 3/2018 |

\* cited by examiner

PARTIAL DEFORMATION MAPS FOR RECONSTRUCTING MOTION-AFFECTED TREATMENT DOSE USING MACHINE LEARNING

CROSS REFERENCE TO RELATED APPLICATIONS

This application claims the benefit of U.S. Provisional Application Ser. No. 62/940,037, filed Nov. 25, 2019, the disclosure of which is incorporated herein by reference in its entirety.

TECHNICAL FIELD

The present disclosure relates to partial deformation maps for reconstructing motion-affected treatment dose, and in particular to systems and methods for generating and utilizing partial deformation maps for reconstructing motion-affected treatment using machine learning.

BACKGROUND

In radiation treatment, doses of radiation delivered via a radiation treatment beam from a source outside a patient's body are delivered to a target region in the body, in order to destroy tumorous cells. Care must be taken to minimize the amount of radiation that is delivered to non-treatment regions while maximizing the amount of radiation delivered by a treatment dose to the intended treatment regions.

BRIEF DESCRIPTION OF THE DRAWINGS

The present disclosure will be understood more fully from the detailed description given below and from the accompanying drawings of various implementations of the disclosure.

DETAILED DESCRIPTION

Figure 1A:
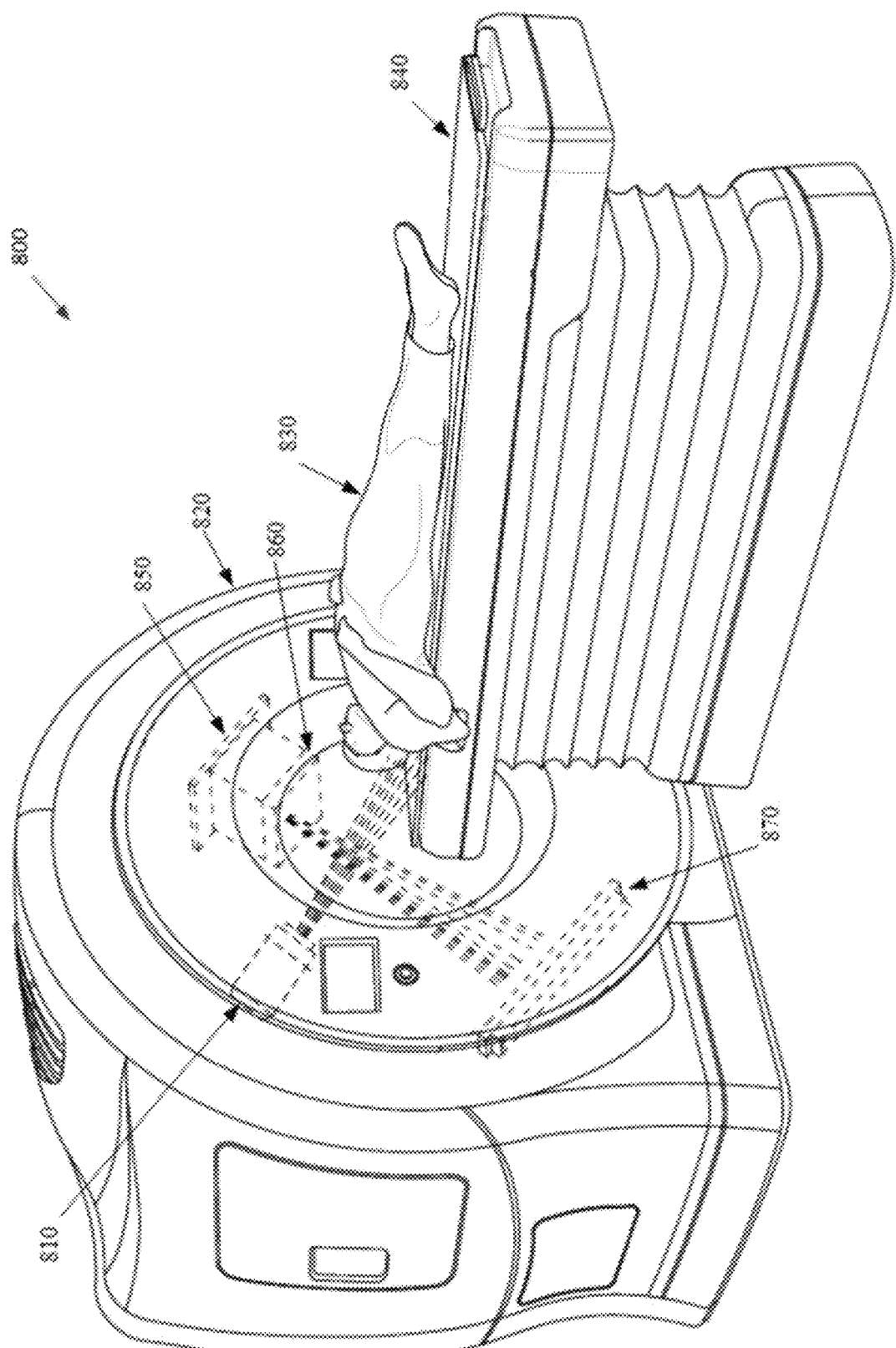
FIG. 1A illustrates a helical radiation delivery system, in accordance with embodiments described herein.

Embodiments of the present invention relate to the field of image guided treatment and, in particular, to a system for partial deformation maps for reconstructing motion-affected treatment using machine learning technologies. In various embodiments, the systems and methods provided herein describe generation and use of intra-patient transformation models from a single image for radiation therapy applications and reducing the effects of appearance changes on registration by generative image metamorphosis.

In one embodiment, a component of radiation treatment therapy may be estimating a transformation between the space of the planning image and that of the patient at treatment time. Ideally, this transformation could be obtainable at treatment time from some limited, low-latency sentinel information, such as 2-D projection images or optical marker positions, so that the transformation can be temporally accurate. Such transformations may be valuable to online adaptation in many forms, specifically with target tracking, dose accumulation, and predictive planning. In fact, if one has a good patient specific transformation model, the image analysis portion of adaptive radiotherapy may be solved.

In one embodiment, a credible transformation that can be determined from 2-D projections at treatment time may be describable by a small number of parameters (e.g., otherwise there may exist many possible transformations which would imply the same projections), and the space spanned by those parameters may consist of credible transformations (e.g., so that unlikely transformations are excluded from the search space). For example, if the transformation model describes respiration, all reasonable parameter choices should produce credible respirations. In sites affected by respiration, such models may be constructed using principal component analysis (PCA) amongst the phases of a respiration correlated computer tomography (RCCT). Similarly, registration of rigid and otherwise linear transformations, which have a small number of degrees of freedom by construction, may also be demonstrated.

In one embodiment, for respiratory motion models, the information used for model construction can be determined at planning time from an RCCT. This may not be the case for other sites, such as the pelvis, where transformations are observed over inter-fractional timescales. Furthermore, respiratory models may also be affected by these inter-fractional transformations, and the accuracy of such respiratory motion models and RCCTs in general may be subpar. Ideally, such a model would be constructible from a single planning image based on transformations observed in similar images and generalizable to likely transformations that the patient may undergo.

In one embodiment, a simple motion model can be constructed as follows: register all images together to form a somehow centrally located "mean" image and a set of transformations from the mean image to each of the phase images and perform PCA directly on the displacement vector fields produced by the group-wise registration. This results in a mean displacement vector $\mu$ and N eigenvectors v such that the linear combination of the first few eigenvectors well approximates all the transformations in the training set.

Considering the parameters as multipliers on the linear combination of the first 1-3 eigenvectors (the sum resulting in a displacement vector field) may produce a reasonable and credible patient specific respiration model with 1-3 parameters. These eigenvectors may be known as modes of variation. In one embodiment, a similar process may not be used for the male pelvis because the transformations are more complex than can be learned from a reasonable number of patient images. It is possible to construct a patient specific transformation model for the male pelvis, but the procedure above may not be successful in some situations. To resolve this problem and reduce the engineering complexity of this approach, there is a desire to combine transformation information from multiple patients into a single site-specific transformation model, which can then be applied to novel patients.

In one embodiment, to construct multi-patient transformation models, PCA models from several patients may be registered to a common atlas space, combined there, and then re-registered to a novel patient. In one embodiment, when modes of variation are transformed across the space of patient transformations to a common space, they undergo an unknown change.

While it is, or may be, possible to describe patient-specific transformation models with a linear dimensionality reduction, the failure of the previous approach suggests that the solution to the transport problem is non-linear.

This disclosure proposes a solution to this registration problem where, given a single patient planning image, a transformation model may be produced, which generates credible non-rigid transformations of that planning image that are likely to be observed over the course of treatment, such that the parameters of the transformation model (and thus the transformation) can be determined from a small number of 2-D projections.

The approach described herein attempts to avoid solving the above problems by providing example data and using neural network topology known as an auto-encoder, which is both suitable for dimensionality reduction and adequately generative. That is, autoencoders may be suitable both for finding low dimensionality representations of data (reduction) and reconstructing that data from the low dimensionality representation (generation). This generation is not always available with non-linear dimensionality reconstruction methods, which makes autoencoders well suited for this problem.

In one embodiment, the terms "target," "target region," "target subject," etc. may refer to one or more fiducials near (within some defined proximity to) a treatment area (e.g., a tumor). In another embodiment, a target may be a bony structure. In yet another embodiment a target may refer to soft tissue of a patient. A target may be any defined structure or area capable of being identified and tracked (including the entirety of the patient themselves) as described herein.

FIG. 1A illustrates a helical radiation delivery system 800 in accordance with embodiments of the present disclosure. The helical radiation delivery system 800 may include a linear accelerator (LINAC) 850 mounted to a ring gantry 820. The LINAC 850 may be used to generate a radiation beam (i.e., treatment beam) by directing an electron beam towards an x-ray emitting target. The treatment beam may deliver radiation to a target region (i.e., a tumor). The treatment system further includes a multileaf collimator (MLC) 860 coupled with the distal end of the LINAC 850. The MLC 860 may be an eMLC, as described herein. The MLC includes a housing that houses multiple leaves that are movable to adjust an aperture of the MLC to enable shaping of the treatment beam. The ring gantry 820 has a toroidal shape in which the patient 830 extends through a bore of the ring/toroid and the LINAC 850 is mounted on the perimeter of the ring and rotates about the axis passing through the center to irradiate a target region with beams delivered from one or more angles around the patient. During treatment, the patient 830 may be simultaneously moved through the bore of the gantry on a treatment couch 840.

The helical radiation delivery system 800 includes an imaging system, comprising the LINAC 850 as an imaging source and an x-ray detector 870. The LINAC 850 may be used to generate a mega-voltage x-ray image (MVCT) of a region of interest (ROI) of patient 830 by directing a sequence of x-ray beams at the ROI which are incident on the x-ray detector 870 opposite the LINAC 850 to image the patient 830 for setup and generate pre-treatment images. In one embodiment, the helical radiation delivery system 800 may also include a secondary imaging system consisting of a kV imaging source 810 mounted orthogonally relative to the LINAC 850 (e.g., separated by 90 degrees) on the ring gantry 820 and may be aligned to project an imaging x-ray beam at a target region and to illuminate an imaging plane of a detector after passing through the patient 130.

Figure 1B:
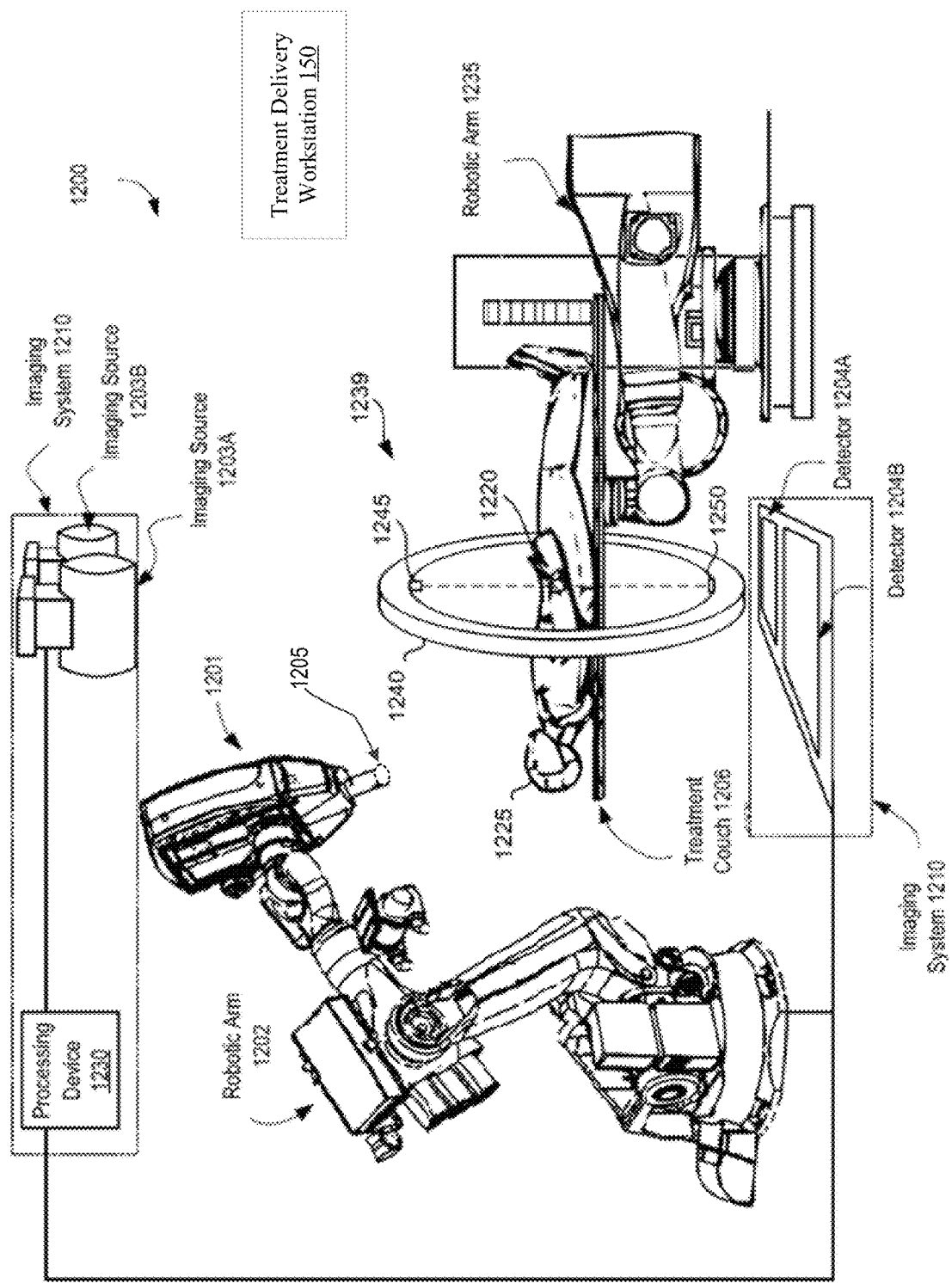
FIG. 1B illustrates a robotic radiation treatment system that may be used in accordance with embodiments described herein.

FIG. 1B illustrates a radiation treatment system 1200 that may be used in accordance with alternative embodiments described herein. As shown, FIG. 1B illustrates a configuration of a radiation treatment system 1200. In the illustrated embodiments, the radiation treatment system 1200 includes a linear accelerator (LINAC) 1201 that acts as a radiation treatment source and an MLC 1205 (e.g., an eMLC) coupled with the distal end of the LINAC 1201 to shape the treatment beam. In one embodiment, the LINAC 1201 is mounted on the end of a robotic arm 1202 having multiple (e.g., 5 or more) degrees of freedom in order to position the LINAC 1201 to irradiate a pathological anatomy (e.g., target) with beams delivered from many angles, in many planes, in an operating volume around a patient. Treatment may involve beam paths with a single isocenter, multiple isocenters, or with a non-isocentric approach.

LINAC 1201 may be positioned at multiple different nodes (predefined positions at which the LINAC 1201 is stopped and radiation may be delivered) during treatment by moving the robotic arm 1202. At the nodes, the LINAC 1201 can deliver one or more radiation treatment beams to a target, where the radiation beam shape is determined by the leaf positions in the MLC 1205. The nodes may be arranged in an approximately spherical distribution about a patient. The particular number of nodes and the number of treatment beams applied at each node may vary as a function of the location and type of pathological anatomy to be treated.

In another embodiment, the robotic arm 1202 and LINAC 1201 at its end may be in continuous motion between nodes while radiation is being delivered. The radiation beam shape and 2-D intensity map is determined by rapid motion of the leaves in the MLC 1205 during the continuous motion of the LINAC 1201.

The radiation treatment system 1200 includes an imaging system 1210 having a processing device 1230 connected with x-ray sources 1203A and 1203B (i.e., imaging sources) and fixed x-ray detectors 1204A and 1204B. Alternatively, the x-ray sources 1203A, 1203B and/or x-ray detectors 1204A, 1204B may be mobile, in which case they may be repositioned to maintain alignment with the target, or alternatively to image the target from different orientations or to acquire many x-ray images and reconstruct a three-dimensional (3-D) cone-beam CT. In one embodiment, the x-ray sources are not point sources, but rather x-ray source arrays, as would be appreciated by the skilled artisan. In one embodiment, LINAC 1201 serves as an imaging source, where the LINAC power level is reduced to acceptable levels for imaging.

Imaging system 1210 may perform computed tomography (CT) such as cone beam CT or helical megavoltage computed tomography (MVCT), and images generated by imaging system 1210 may be two-dimensional (2-D) or three-dimensional (3-D). The two x-ray sources 1203A and 1203B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 1206 during treatment) and to illuminate imaging planes of respective detectors 1204A and 1204B after passing through the patient. In one embodiment, imaging system 1210 provides stereoscopic imaging of a target and the surrounding volume of interest (VOI).

In other embodiments, imaging system 1210 may include more or less than two x-ray sources and more or less than two detectors, and any of the detectors may be movable rather than fixed. In yet other embodiments, the positions of the x-ray sources and the detectors may be interchanged. Detectors 1204A and 1204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3-D CT image based on simulating the x-ray image formation process by casting rays through the CT image.

In one embodiment, IGRT delivery system 1200 also includes a secondary imaging system 1239. Imaging system 1239 is a Cone Beam Computed Tomography (CBCT) imaging system, for example, the medPhoton ImagingRing System. Alternatively, other types of volumetric imaging systems may be used. The secondary imaging system 1239 includes a rotatable gantry 1240 (e.g., a ring) attached to an arm and rail system (not shown) that move the rotatable gantry 1240 along one or more axes (e.g., along an axis that extends from a head to a foot of the treatment couch 1206. An imaging source 1245 and a detector 1250 are mounted to the rotatable gantry 1240.

The rotatable gantry 1240 may rotate 360 degrees about the axis that extends from the head to the foot of the treatment couch. Accordingly, the imaging source 1245 and detector 1250 may be positioned at numerous different angles. In one embodiment, the imaging source 1245 is an x-ray source and the detector 1250 is an x-ray detector. In one embodiment, the secondary imaging system 1239 includes two rings that are separately rotatable. The imaging source 1245 may be mounted to a first ring and the detector 1250 may be mounted to a second ring. In one embodiment, the rotatable gantry 1240 rests at a foot of the treatment couch during radiation treatment delivery to avoid collisions with the robotic arm 1202.

As shown in FIG. 1B, the image-guided radiation treatment system 1200 may further be associated with a treatment delivery workstation 150. The treatment delivery workstation may be remotely located from the radiation treatment system 1200 in a different room than the treatment room in which the radiation treatment system 1200 and patient are located. The treatment delivery workstation 150 may include a processing device (which may be processing device 1230 or another processing device) and memory that modify a treatment delivery to the patient 1225 based on a detection of a target motion that is based on one or more image registrations, as described herein.

Figure 1C:
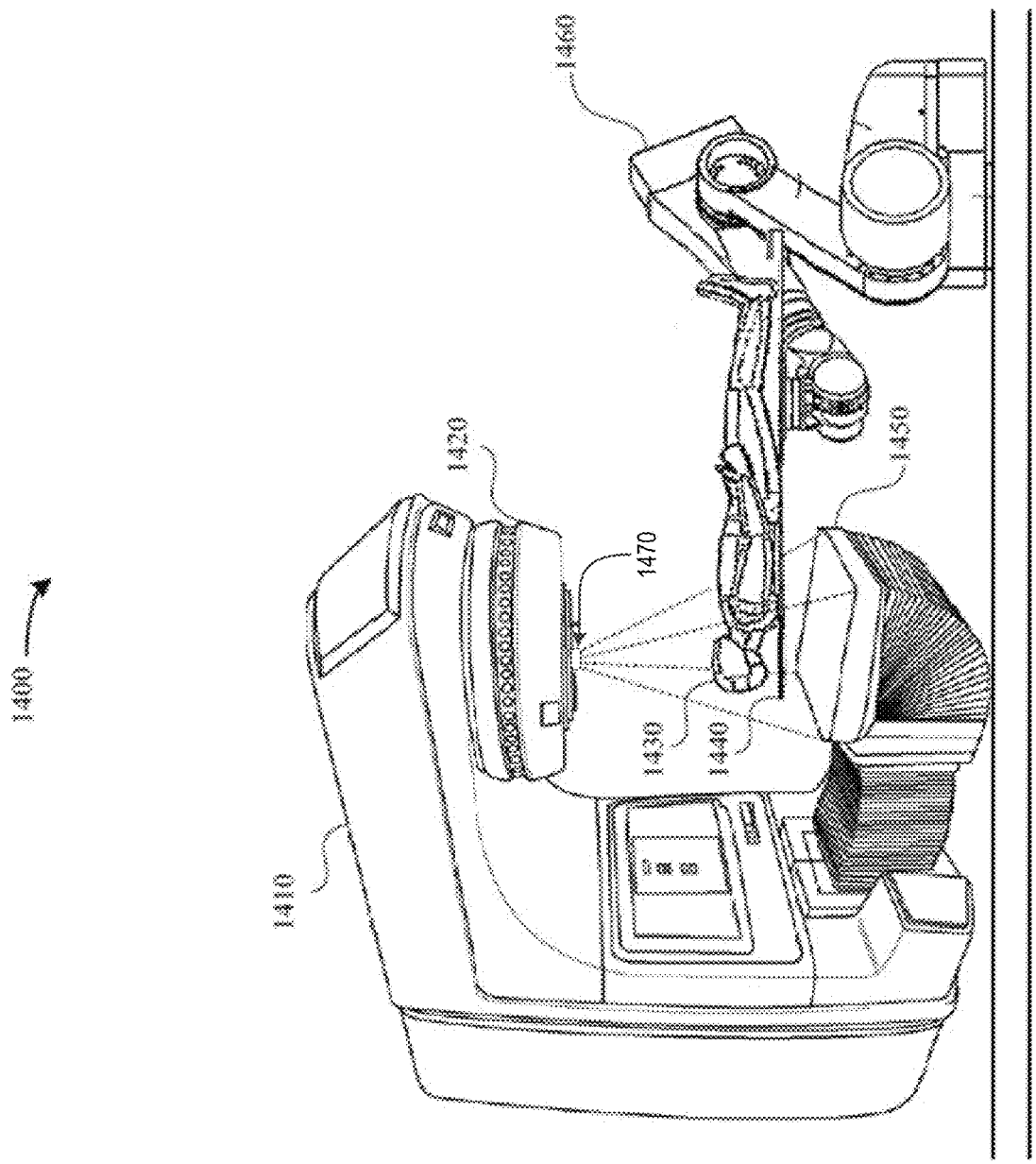
FIG. 1C illustrates a C-arm gantry-based radiation treatment system, in accordance with embodiments described herein.

FIG. 1C Illustrates a C-arm radiation delivery system 1400. In one embodiment, in the C-arm system 1400 the beam energy of a LINAC may be adjusted during treatment and may allow the LINAC to be used for both x-ray imaging and radiation treatment. In another embodiment, the system 1400 may include an onboard kV imaging system to generate x-ray images and a separate LINAC to generate the higher energy therapeutic radiation beams. The system 1400 includes a gantry 1410, a LINAC 1420, an MLC 1470 (e.g., an eMLC) coupled with the distal end of the LINAC 1420 to shape the beam, and a portal imaging detector 1450. The gantry 1410 may be rotated to an angle corresponding to a selected projection and used to acquire an x-ray image of a VOI of a patient 1430 on a treatment couch 1440.

In embodiments that include a portal imaging system, the LINAC 1420 may generate an x-ray beam that passes through the target of the patient 1430 and are incident on the portal imaging detector 1450, creating an x-ray image of the target. After the x-ray image of the target has been generated, the beam energy of the LINAC 1420 may be increased so the LINAC 1420 may generate a radiation beam to treat a target region of the patient 1430. In another embodiment, the kV imaging system may generate an x-ray beam that passes through the target of the patient 1430, creating an x-ray image of the target. In some embodiments, the portal imaging system may acquire portal images during the delivery of a treatment. The portal imaging detector 1450 may measure the exit radiation fluence after the beam passes through the patient 1430. This may enable internal or external fiducials or pieces of anatomy (e.g., a tumor or bone) to be localized within the portal images.

Alternatively, the kV imaging source or portal imager and methods of operations described herein may be used with yet other types of gantry-based systems. In some gantry-based systems, the gantry rotates the kV imaging source and LINAC around an axis passing through the isocenter. Gantry-based systems include ring gantries having generally toroidal shapes in which the patient's body extends through the bore of the ring/toroid, and the kV imaging source and LINAC are mounted on the perimeter of the ring and rotates about the axis passing through the isocenter.

Gantry-based systems may further include C-arm gantries, in which the kV imaging source and LINAC are mounted, in a cantilever-like manner, over and rotates about the axis passing through the isocenter. In another embodiment, the kV imaging source and LINAC may be used in a robotic arm-based system, which includes a robotic arm to which the kV imaging source and LINAC are mounted as discussed above. Aspects of the present disclosure may further be used in other such systems such as a gantry-based LINAC system, static imaging systems associated with radiation therapy and radiosurgery, proton therapy systems using an integrated image guidance, interventional radiology and intraoperative x-ray imaging systems, etc.

With respect to the systems described above and herein, in one embodiment, a radiation treatment delivery system (e.g., of any suitable type) may include a memory to store a treatment planning image of a target subject and a processing device, operatively coupled to the memory. In the various embodiments described herein, the processing device may perform a variety of operations. For example, the processing device may: input the treatment planning image of the target subject into a machine learning system; determine, by the machine learning system, a first target-subject-specific model of the treatment planning image; apply the first target-subject-specific model to the treatment planning image to generate a transformed treatment planning image corresponding to a first position of a plurality of positions of the target subject; compare the transformed treatment planning image to a reference image; based on the comparing, modify one or more parameters of the first target-subject-specific model to generate a second target-subject-specific model corresponding to a second position of the plurality of positions; and control a treatment device based on the second target-subject-specific model to deliver a treatment to the target subject.

In one embodiment, the treatment planning image is one of 3-D or 4-D anatomical images and wherein the transformed treatment planning image and the reference image are 2-D images. In one embodiment, the machine learning system is trained to construct the first target-subject-specific model from a 3-D, 4-D, or other derived image of the target subject. In one embodiment, the machine learning system is trained to construct the first target-subject-specific model from at least one deformable registration between the target subject and another subject. In one embodiment, the machine learning system is trained to construct the first target-subject-specific model from at least one deformable registration between the target subject at a first time and the target subject at a second time. In one embodiment, the machine learning system is trained to construct the first target-subject-specific model from at least one deformable registration between the target subject and a synthesized atlas subject. In one embodiment, the machine learning system uses a population of training subjects and a plurality of images associated with each of a plurality of training subjects as training data. In one embodiment, the machine learning system uses calculated subject-specific models as training data.

In one embodiment, the subject-specific models comprise a central atlas of the target subject and a set of basis transformations and appearance changes that are combined linearly to produce an estimate of one or more conformations in which the target subject may be found. In one embodiment, the subject-specific models comprise a model synthesis function comprising at least one of: linear combinations of basis functions or neural networks. In one embodiment, the subject-specific models are developed from dimensionality reduction on a set of at least one of: real or synthetic data. In one embodiment, the machine learning system uses a generative adversarial network that produces subject-specific models as its output. In one embodiment, the machine learning system uses an autoencoder network from which a decoder component can be used as the first subject-specific model. In one embodiment, the machine learning system uses transfer learning from a system that produces subject-specific models from a subject to produce subject-specific models for another subject. In one embodiment, the processing device is further to receive an auxiliary anatomical or pseudo-anatomical signal, wherein the auxiliary signal is obtained optically based on a set of triangulated light-emitting diode (LED) markers.

As described herein, the radiation treatment system may optionally include a gantry coupled to the radiation source, wherein the gantry is configured to rotate the radiation source about the target subject. In one embodiment, the gantry includes a C-arm gantry. In another embodiment, the gantry includes a ring gantry. The radiation treatment system may optionally include a robotic arm coupled to the radiation source. In one embodiment, the robotic arm is configured to position the radiation source at a plurality of positions along a circular or elliptical trajectory. In one embodiment, the robotic arm positions the radiation source at the plurality of positions about the target subject. The radiation beam (e.g., from the radiation source) may include a kilovolt (kV) treatment beam. The MLC may include a binary MLC. Any other suitable combinations of equipment and functionality are further contemplated herein.

Figure 2A:
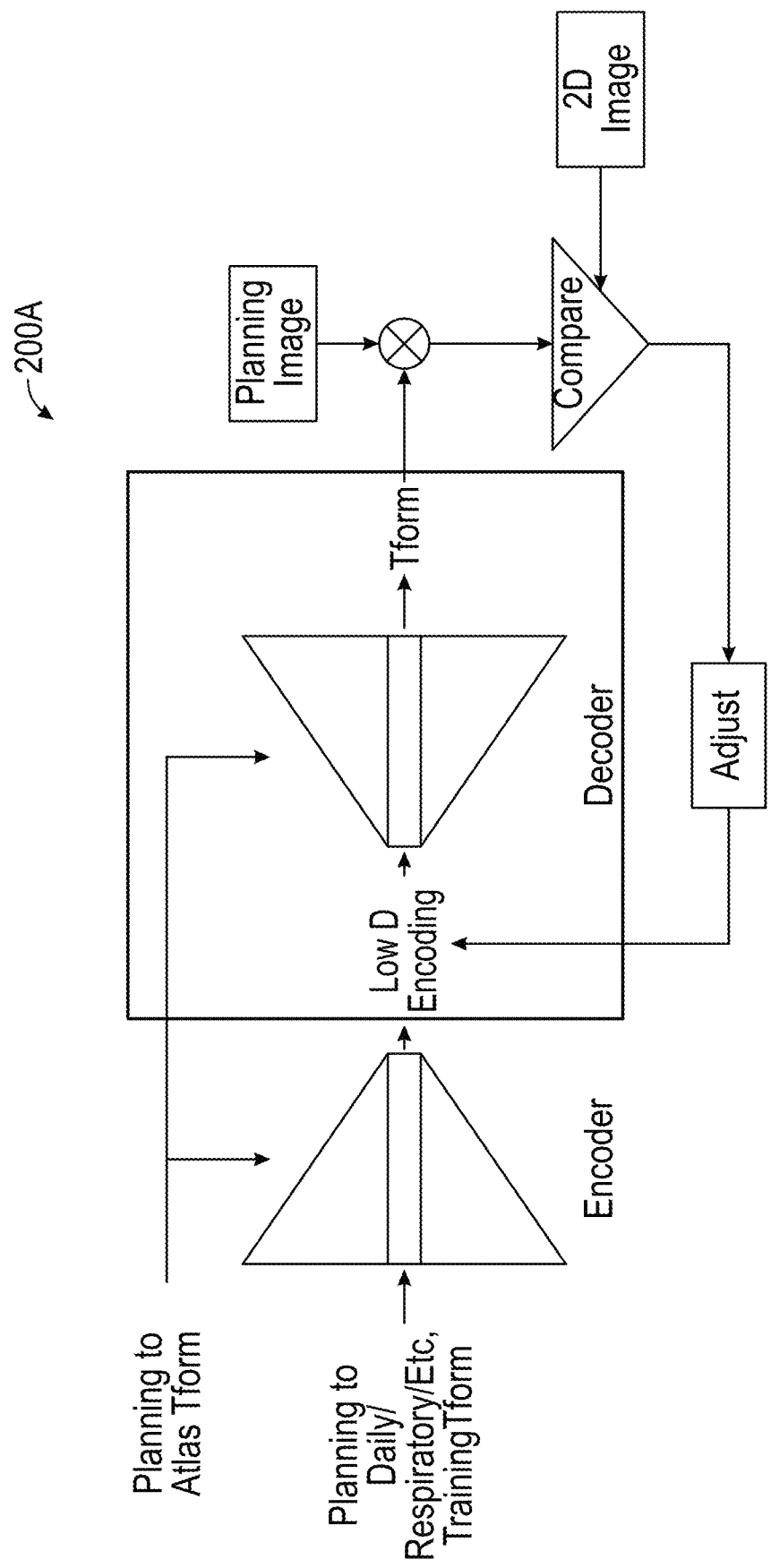
FIG. 2A depicts a flow diagram of a method of an autoencoder and 2-D/3-D registration, in accordance with embodiments of the disclosure.

FIG. 2A depicts a flow diagram of a method 200A of an autoencoder and 2-D/3-D registration, in accordance with embodiments of the disclosure. In general, each of the methods described herein (including method 200A) may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the methods may be performed by processing logic of the radiation treatment system 800 of FIG. 1A.

In one embodiment, an autoencoder is a neural network that receives an input and produces a small number of parameters as output. To train this network, the encoder may be paired with a decoder that receives those small number of parameters and attempts to reproduce the input data. In one embodiment of the current disclosure, after training, the encoder may be discarded, and the decoder alone may be used to perform registration. A 3-D/2-D optimization may then be performed by comparing DRRs of the transformed planning image with measured 2-D projections. This is shown FIG. 2A.

As described herein, an encoder/decoder pair may find a low dimensionality representation of the data. In principle, this should reduce overfitting since any low dimensionality representation that thoroughly represents the training data must inherently consist of meaningful parameters. This, plus a proper amount of training data and careful construction of the network, may ensure that the model generalizes.

In one embodiment, the planning to atlas transformation may be auxiliary data that attempts to reduce variation in the training data and retrofit the network into learning the model in a common space. That is, the network should do something with the planning to daily transformation, transform that to the common space, do something else, and produce a low dimensionality encoding. Decoding is the inverse of this process. One benefit of this transformation as input data is that it can be obtained from the single planning image.

In one embodiment, FIG. 2A illustrates the application of the decoder to 3-D/2-D registration. As training input, it receives a set of planning to daily images from some number of patients and attempts to learn to reproduce those transformations. This is a good first step (or perhaps initialization) and may produce good transformations. In other embodiments, this concept may be further generalized. For example, in one non-limiting embodiment, instead of using the network to learn a set of provided transformations, the network may perform the registrations itself. That is, given input as the planning image and transformation from planning image to an atlas space, the parameters of the network could be adjusted so that the output of the network is the transformation without invoking an external registration method. This may limit any bias imposed by the initial registration and makes the learning process a registration itself.

Figure 2B:
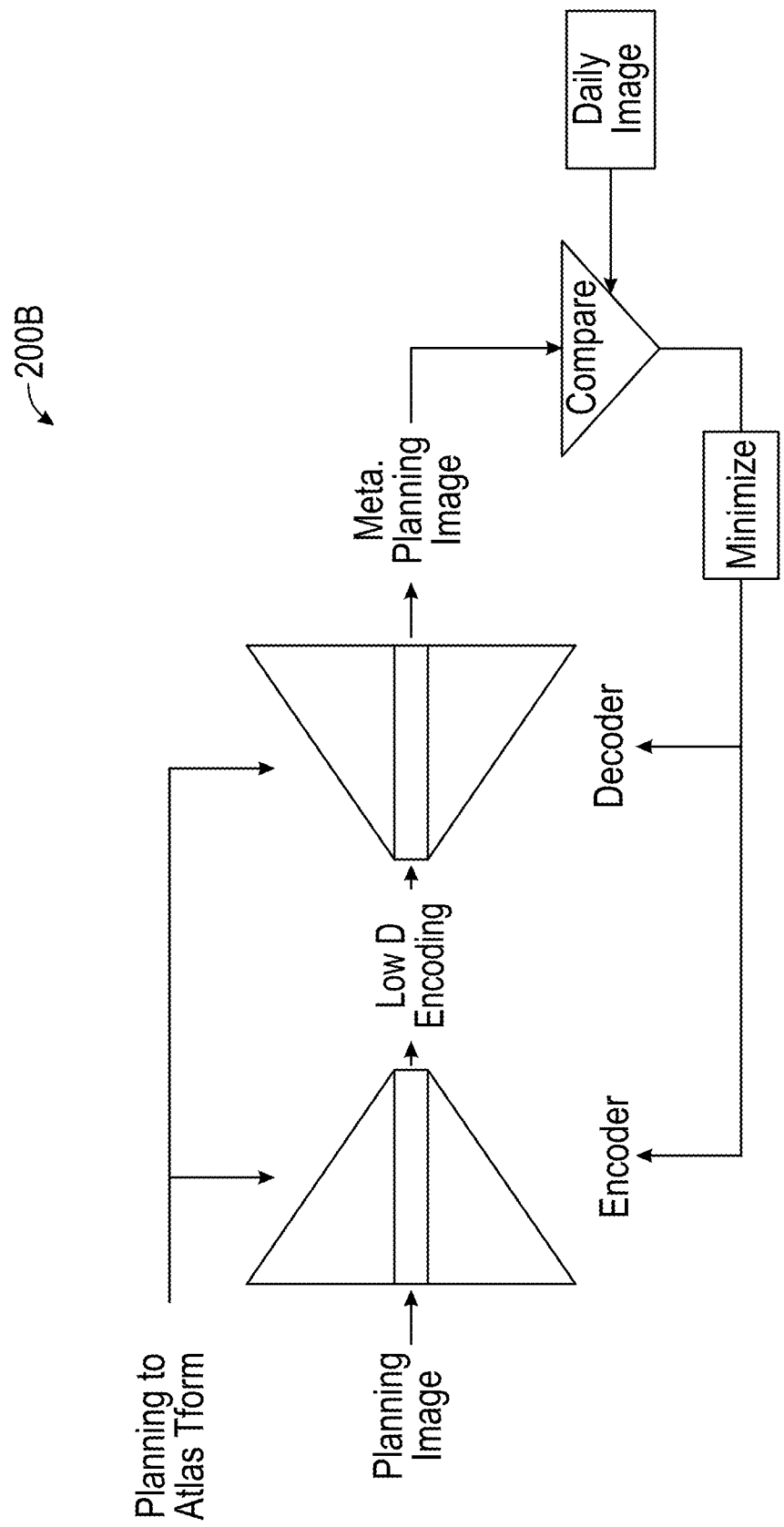
FIG. 2B depicts a flow diagram of a method of an autoencoder network learning a low dimensionality metamorphosis of a planning image, in accordance with embodiments of the disclosure.

In one embodiment, in addition to the transformation, the network may also produce a metamorphosed image. That is, the low dimensionality encoding could represent appearance changes to the image, such as the presence of gas in the rectum, in addition to the transformation. This metamorphosis approach may require additional data. In one embodiment, a similar autoencoder approach to the one described above may produce metamorphosed images and transformations in a completely unsupervised, training data-free way that could resolve 3-D/3-D registration issues caused by these appearance changes, since the autoencoder training process is in fact a registration. An illustration of a method 200B of both approaches is shown in FIG. 2B.

Figure 3A:
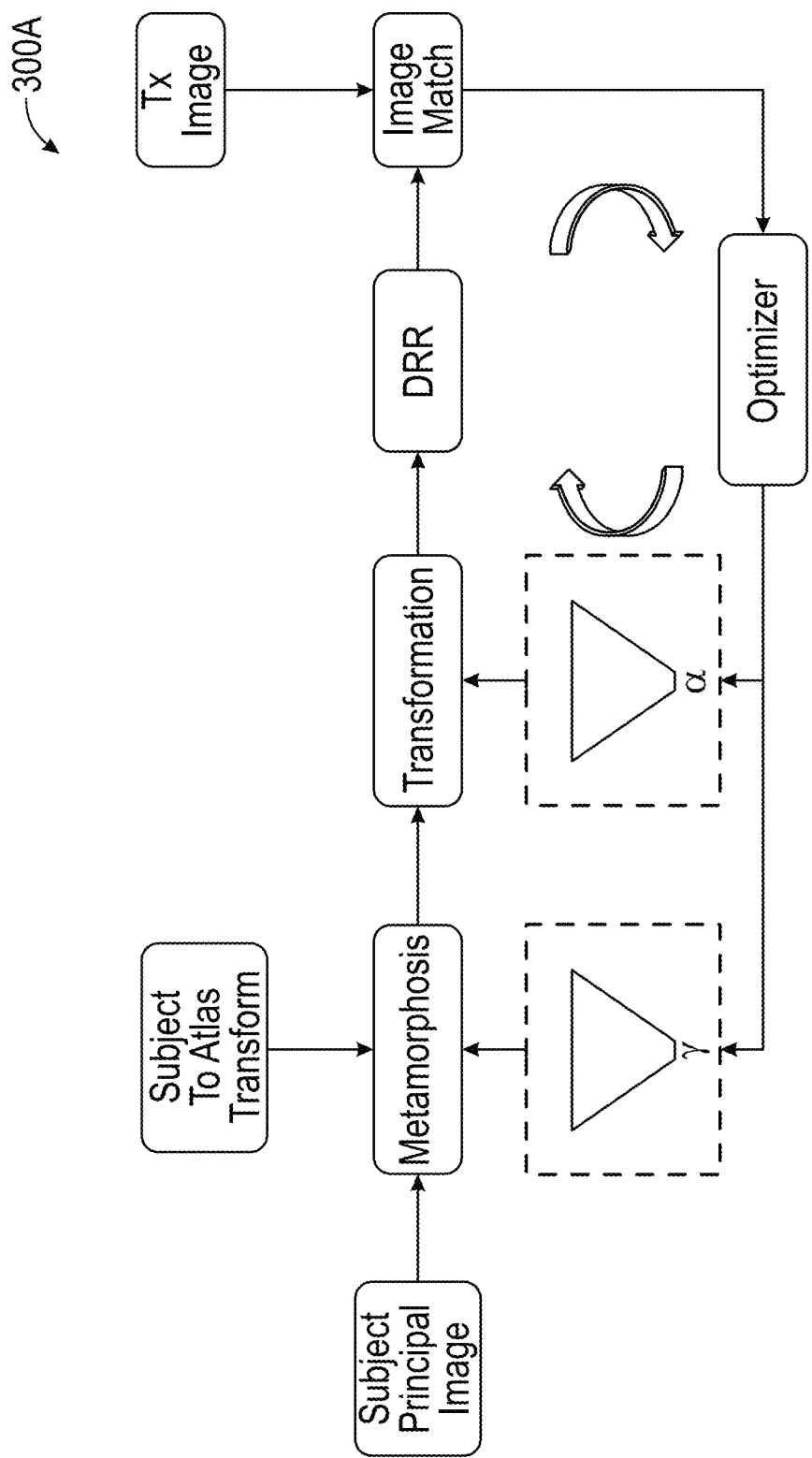
FIG. 3A depicts a flow diagram of a general machine-learning method, in accordance with embodiments of the disclosure.

FIG. 3A depicts a flow diagram of a general machine-learning method 300A, in accordance with embodiments of the disclosure. In one embodiment, one goal of this method 300A involves registering a subject to some treatment time image—in this non-limiting example a planar x-ray image—in order to find a transformation between the subject at some time and the subject at another time. Because the general registration problem is underdetermined, the space of possible solutions should be reduced in order to find a correct solution. In the example shown in FIG. 3A, some image of the subject is metamorphosized (i.e. the intensity values of the image are changed) according to a low dimensionality representation of possible such changes. That image is then transformed geometrically according to a low dimensionality geometric transformation model. That image is then used to generate a DRR by simulating the process of x-ray imaging. The DRR may then be compared with an actual, measured radiograph. The parameters of the models may then be optimized such that the DRR of the transformed and metamorphosized image matches the actual x-ray as much as possible (e.g., within a defined threshold). Many variations on this are possible. Several possible ways to obtain these models and variations on the method are explained below.

Figure 3B:
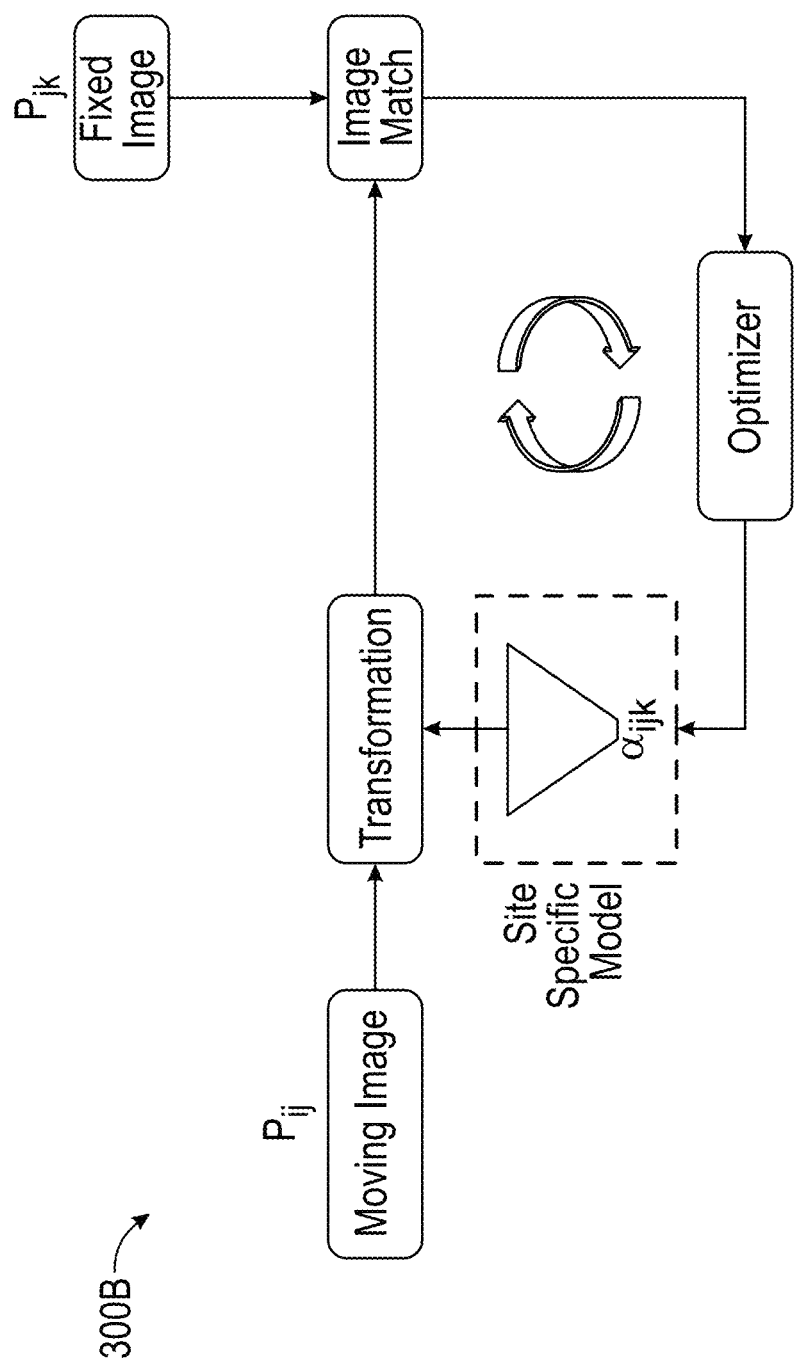
FIG. 3B depicts a flow diagram of learning a model using a direct method, in accordance with embodiments of the disclosure.

FIG. 3B depicts a flow diagram of learning a model using a direct method 300B, in accordance with embodiments of the disclosure. In one embodiment, the parameters of the direct method 300B may be the coefficients and meta parameters of the site-specific model and the input parameters for each patient image pair, $\alpha$. The input data may be intra-subject image pairs. The method minimizes the image match term over the parameters. The site-specific model parameterized by alpha then describes the set of intra-subject transformations that are likely to be observed over a whole population of subjects.

In one embodiment, method 300B may be successful at summarizing human deformations. Indeed, it is provably successful with sufficient training data. While this method may be successful, there may be too much inherent variation in the set of all single site deformations for all (human) subjects for us to construct such a model with a reasonable amount of training data.

Furthermore, the inherent dimensionality of such deformation may be too large for the 3-D-2-D application. That is, in one embodiment, a typical intra-subject respiratory only model should have 2-3 parameters, while a respiratory and whole thorax model may have thousands. This, however, is still superior to the millions of parameters that are typically used for a general registration problem. The application shown in 3A suggests that the model only parameterize likely deformations for a single subject in order that only likely deformations are accessible. If this restriction is not made, it is extremely unlikely that any transformation that is found is a correct one.

In one embodiment, a naïve implementation of this method may expect hundreds of subjects each with several images, leading to a total of 10s of thousands of image pairs. A typical image registration loop of transform→match→optimize might be executed hundreds of times for each subject. As such, a bootstrapping method is proposed below, where an initial site-specific model is built from a more limited data set which is then refined.

Figure 3C:
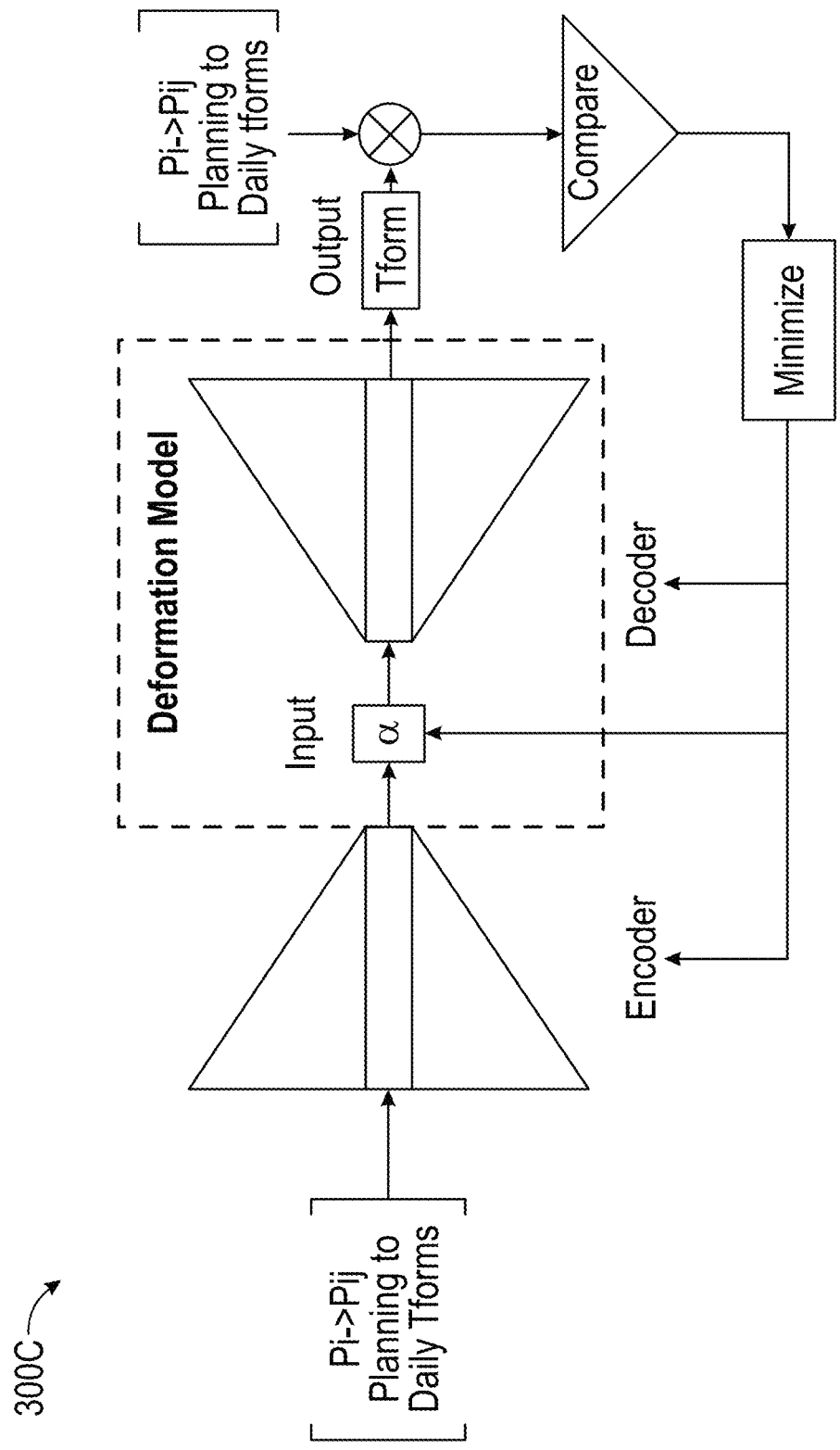
FIG. 3C depicts a flow diagram of learning a model using a bootstrapping method, in accordance with embodiments of the disclosure.

FIG. 3C depicts a flow diagram of learning a model using a bootstrapping method 300C, in accordance with embodiments of the disclosure. In one embodiment, one objective of the present disclosure is to provide for low dimensionality representations of sets of likely transformations. Ultimately, the model-building portion of the task may involve the minimization of some image similarity metric over some high dimensional parameterization of a system that is able to produce likely transformations for a subject, which may be used to deform images for evaluation of the image similarity metric. There may exist many different and effective methods for finding transformations outside of a ML framework, either between pairs of images or groups of images. These independently computed transformations may then be used to determine an initial estimate for the parameters of the deformation portion of the ML task. In one embodiment, this may be done by learning feasible transformations with an autoencoder, where the input and output of the network are feasible transformations. The weights for the decoder portion of the autoencoder may then be used to initialize the weights of any further networks, which are then refined. In one embodiment, this may decrease convergence time and reduce failed model builds.

In one embodiment, similarly to the direct method described with respect to 300B, a network trained in this way may be an effective deformation model, but the transformations that it produces may be limited to a space spanned by the training deformations, which may not be the best possible deformations that minimize a hypothetical image similarity metric over a dataset. This may occur because image similarity error information is not included in the bootstrapping optimization. Refining the deformation models by avoiding the discarding of, for example, error information in the summarization process, may provide better models. At the very least, this bootstrapped deformation model will not be made worse during any further learning (provided further learning optimizes over the same image similarity metric used in the construction of the training transformations, which may or may not be the goal).

Figure 4A:
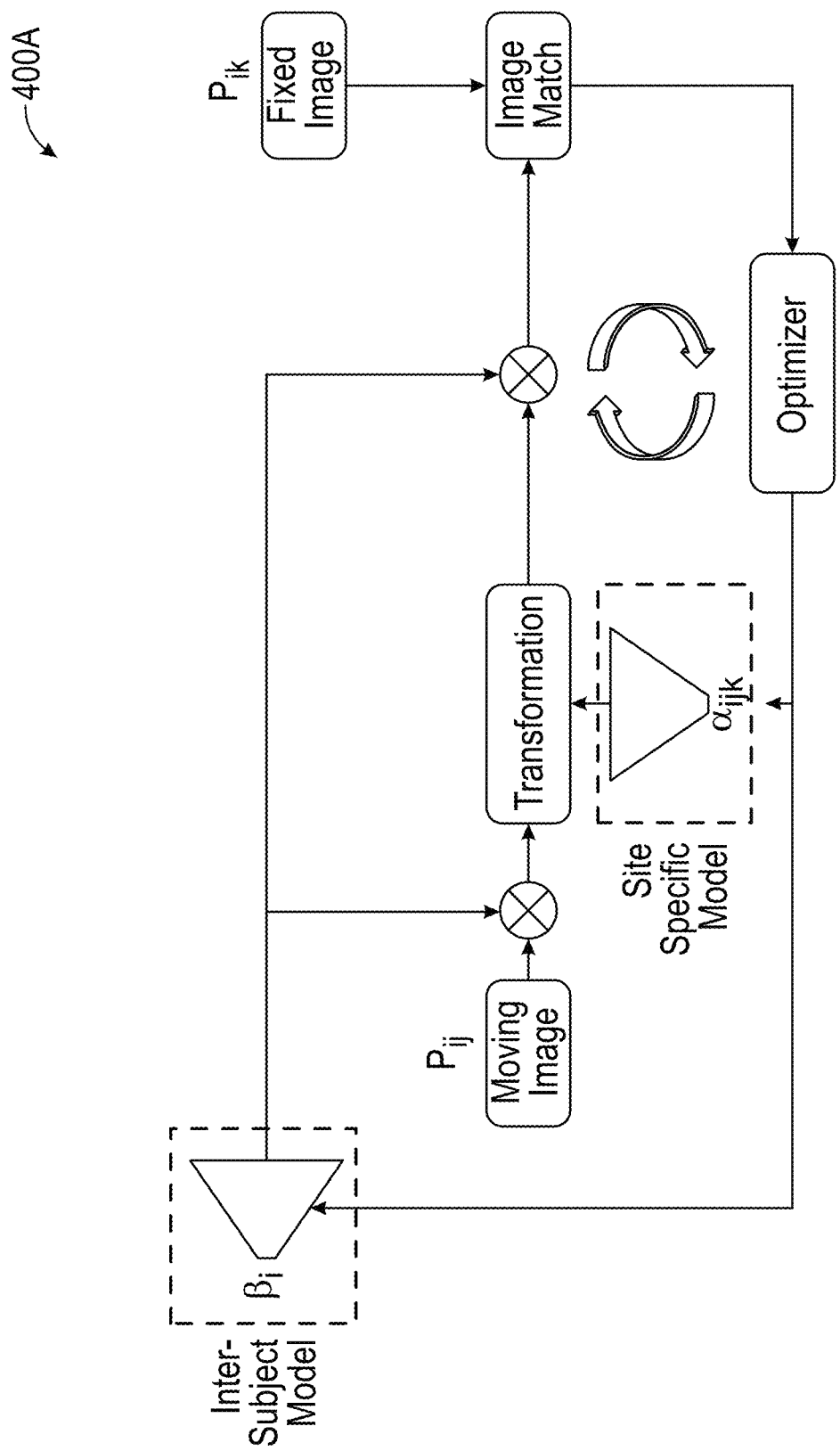
FIG. 4A depicts a flow diagram of learning a model using a separated direct method, in accordance with embodiments of the disclosure.

FIG. 4A depicts a flow diagram of learning a model using a separated direct method 400A, in accordance with embodiments of the disclosure. The previously described direct method 300B builds a deformation model that encompasses both intra-patient changes and inter-patient changes. During learning, the parameters of the inter-subject model $\beta$ remain constant within each patient. These $\beta$ describe a transformation which is applied to the moving image to transform it from the coordinates of an individual subject to a common coordinates of all subjects. There, the parameters a describe a second transformation, in the common coordinates, that is also applied to the moving image. This may be followed by application of the inverse of the inter-subject transformation. The triply transformed image is then in the space of the fixed image, and the image match can be computed and optimized. Similarly, the forward intra-subject transformation could be applied to the fixed image and the image match computed in the common space. The "two transformations" requirement leads to the greatest weakness of this method, which is further described below.

In one embodiment, for a particular subject's treatment, the parameters β can be determined by registration of the inter-subject model with the planning CT and may then remain constant while the parameters a are optimized during treatment with treatment time image data.

To clarify registration of the inter-subject model, each subject may have a set of parameters β that describe a transformation from conformations of that subject to a common space and parameters alpha that describe transformations between conformations of that subject. In order to register a subject image to the inter-subject model using the traditional registration loop, an "atlas" image may be utilized which may be, the average image over the training set. Amongst other possible methods, such an atlas can be constructed as follows: construct a synthetic mean image as the voxel-wise mean of all images in the training set; perform one epoch of training, registering, over the parameters $β_i$ and $α_{ijµ}$, where µ indicates the parameters belong to the registration of image j in patient i with the mean image, each image in the data set with the synthetic mean image; re-compute the mean image using all the images, which are now more aligned; and continue until convergence.

In one embodiment, the mean image may then be used as an atlas and an image from a subject can be deformed to match the atlas image by registering over the parameters α and β. In one embodiment, the method 300D described herein can be called a pair-wise/group-wise method, where the intra-subject deformation model is constructed over pair-wise data (pairs of different images of the same subject) and the inter-subject model is constructed over all of the subjects as a whole. Similarly, the first direct method 300B can be described as pair-wise/pair-wise method.

By analogy, a group-wise/group-wise method can be constructed where, per subject, there is a single mean image. In this case, a mean image may be utilized during learning, where such an image is implicit in the pair-wise/pair-wise method. While this direct method may be effective, it may suffer from two weaknesses. The first is that, while the separated direct method is an improvement over the direct method, in that inter-subject variation does not need to be explained by the model employed at treatment time. That model must still explain intra-subject variation from all subjects—it is not subject specific. Second is that the intra-subject model exists in the common space and any of that set of intra-subject transformations composed with an inter-subject transformation is not likely to be an optimal representation of a specific subject's deformations—it may be better if each subject not only had his or her own intra-subject model but it was also constructed in a coordinate specific to each subject. Many further variations of the methods described here are contemplated in accordance with any suitable image registration practice.

Figure 4B:
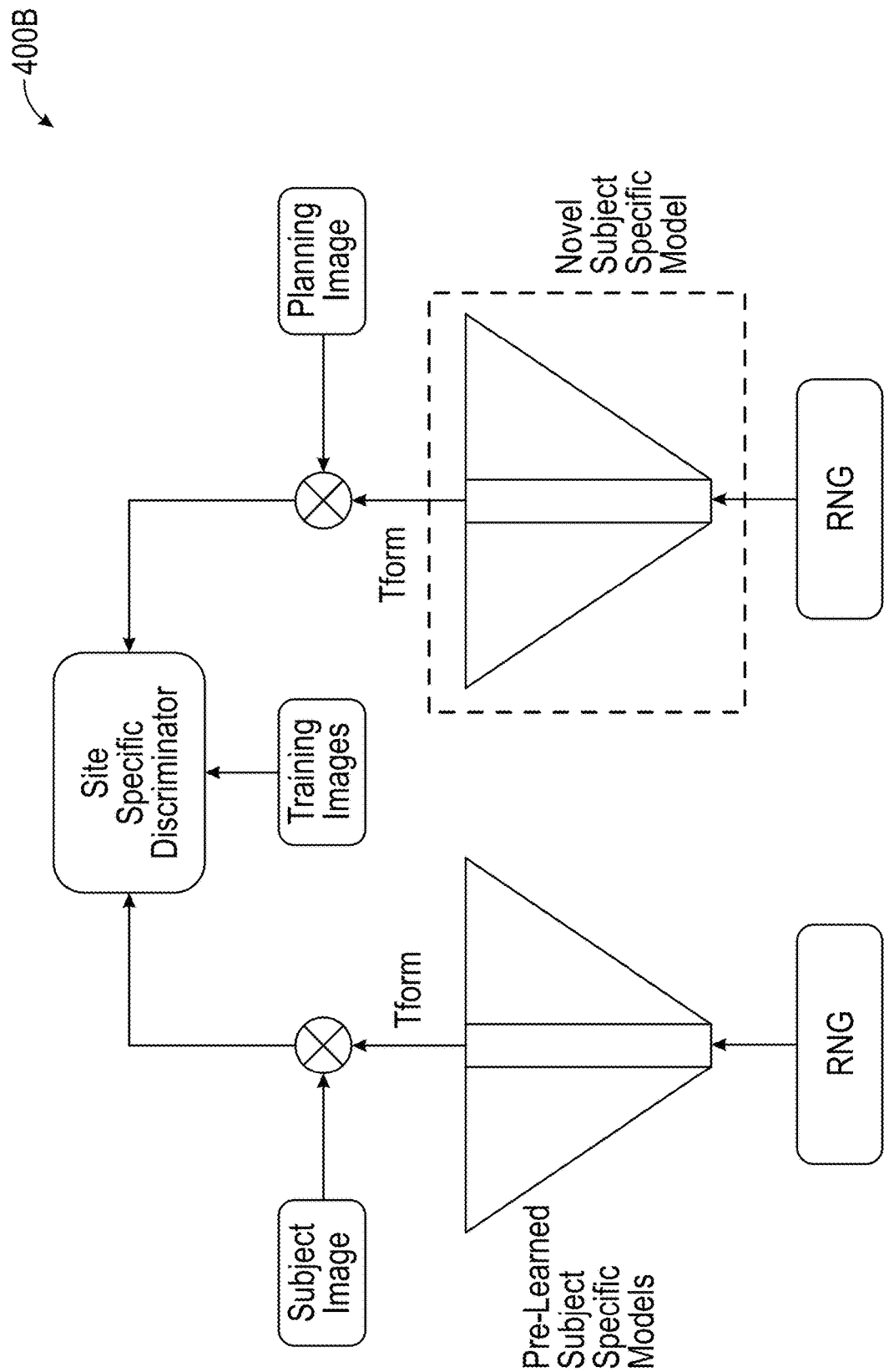
FIG. 4B depicts a flow diagram of learning a model using subject-specific generative adversarial methods, in accordance with embodiments of the disclosure.

FIG. 4B depicts a flow diagram of learning a model using subject-specific generative adversarial (GAN) methods 400B, in accordance with embodiments of the disclosure. In one embodiment, there may be a wide array of variations of the GAN and GAN-like methods where the goal is to generate a subject specific deformation model. An exemplary summary follows.

An embodiment starts with a set of subject specific deformation models used for training. Such models should take in random parameters and produce valid transformations of a subject given some subject images. Such models can be decoders or as simple as linear combinations of basis vectors, where respiratory motion can be shown to be well describable using a PCA model based on group-wise registration of the phases of a respiratory correlated CT with as few as three principal components. One point in support of this method 400B is that each of the subject specific models can be very simple, most of the complexity being in the discriminator.

Figure 4C:
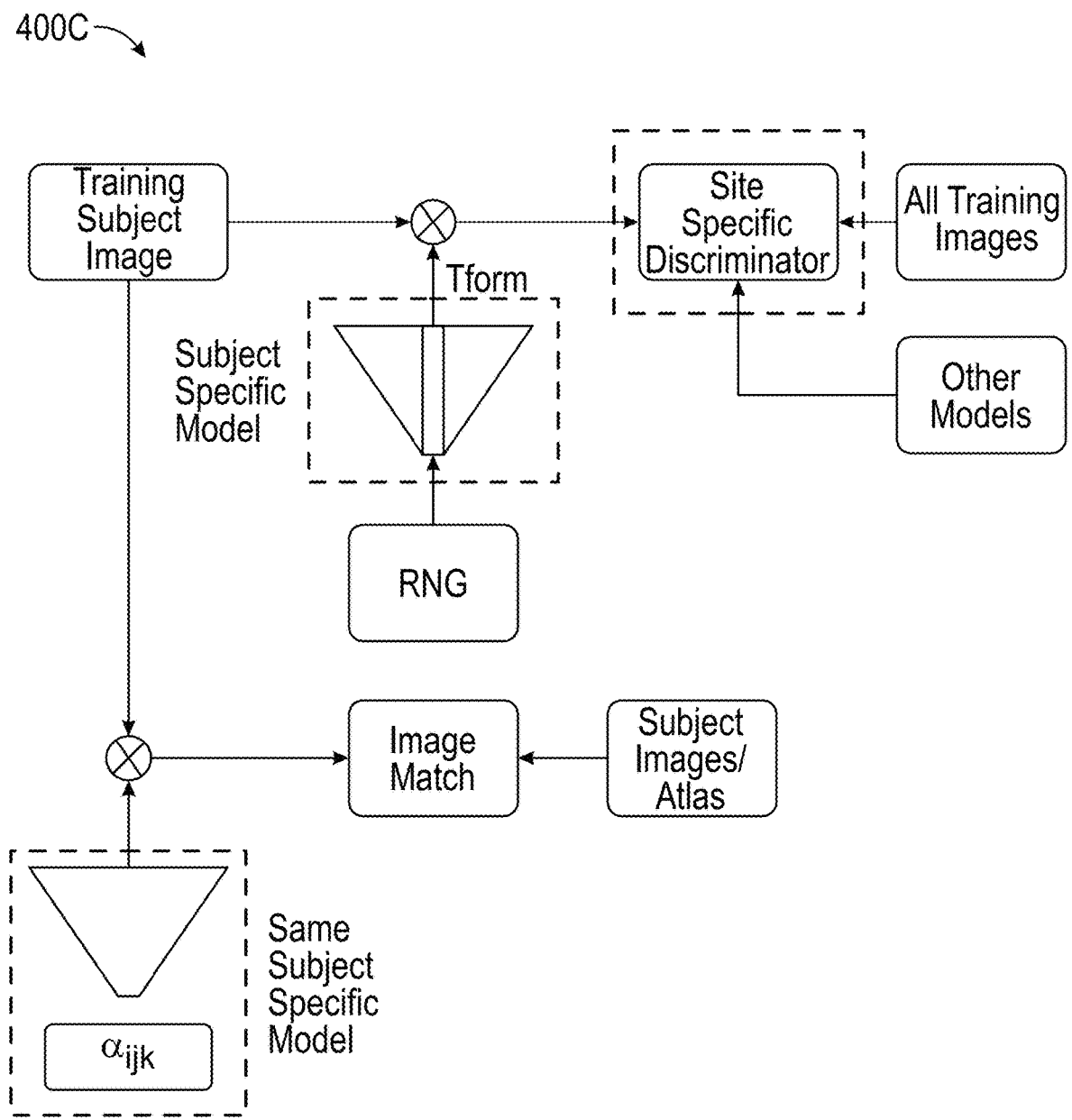
FIG. 4C depicts a flow diagram of learning a model using a GAN-like method with simultaneous model refinement, in accordance with embodiments of the disclosure.

First, during pre-training, subject specific deformation models may be constructed for each of the training subjects—the training models. A discriminator may then be trained by pairing all the training images and training models, feeding the trained models random parameter vectors, and optimizing over the discriminator until the discriminator cannot discriminate between the images generated by the various training models and the real images. A variation may include optimizing over the parameters of the training models during pre-training. This may include simultaneous optimization of the parameters of the training models and the site-specific discriminator with a variant of the same type of learning that is used in the direct method. This is shown in method 3B. In method 3B, both decoders shown are the same. They are shown in a different location in method 400C of FIG. 4C for demonstration purposes.

Other variations may include the discriminator having access to both the un-deformed image as well as the deformed image and possibly any of the various transformations involve (e.g., the planning image to population atlas transformation or the output of the subject specific model) or some representation thereof.

Second, during subject-specific training, a novel subject with a planning image alone is introduced. The parameters of the subject's subject specific deformation model may be optimized until the images it generates can no longer be discriminated from the others (and/or above some pre-defined threshold), at which point the method is done. This could also be considered as a type of transfer learning and innovations in that area may find application here.

In another embodiment, a system may be constructed that knows how to construct a deformation model (e.g., a set of linear deformation bases). In one embodiment, the model may take in an image and produce some pre-specified number of bases that describe motion for that image. For this case, the output data used during training may be a PCA model constructed for the corresponding input image from the subject's training images. This may allow unsupervised separation of model parameters into semantically related modes—for example, a respiratory phase. In other embodiments, the models may also be coerced in to learning this in a semi-supervised fashion.

In some of the methods herein, a subject image (e.g., of a target subject) available prior to treatment is transformed and then compared with an image taken at treatment time. In general, this image may be a measurement of the subject's x-ray attenuation. The target subject's attenuation distribution at planning time may differ from the subject's attenuation at treatment time in two ways: diffeomorphically and non-diffeomorphically. In the former, a smooth deformation can map between the two attenuation distributions. This may account for things like change in pose as well as changes in the subject composition, for example, loss of body mass, edema, change in bladder volume.

In one embodiment, these types of changes may be accounted for by the previously described methods. In the latter, a smooth deformation may not be able to map between the two. These types of changes include changes in bowel and body cavity contents (which may include contents of different density at different locations, such as gas), surgical scarring, implantations (such as clips or catheters), and non-diffeomorphic tumor shape changes. In one embodiment, these types of non-diffeomorphic changes may not be able to be accounted for in a typical registration framework because, 1) the types of transformations estimated are diffeomorphic and 2) there does not generally exist a good image match term that can determine the quality of alignment of two images with such changes. In particular, these can significantly decrease the accuracy of registrations and can be particularly problematic, especially in certain areas—such as the pelvis where bowel contents can change drastically between treatments and are adjacent (and internal to) structures of interest. Furthermore, an application of this work involves the continuous, high-temporal resolution calculation of dose.

In one embodiment, a goal for accurately calculating dose is a high-fidelity representation of an attenuation-like quantity. Previous methods described in this document may estimate geometric transformations. Transformations account for most of variance observed in the population of interest. Estimating these transformations using only an image match term may suffer from the problems described in the previous paragraph leading to increased, un-real, and un-realistic variation present in the population to be explained. For example, the transformation may try to match two gas bubbles in the rectum, resulting in large deformations when transformation of the rectal contents is completely unimportant. In one embodiment, only certain changes can be observed. For example, air bubbles may be found in the rectum but may not (typically) be found in a subcutaneous fat layer.

Figure 4D:
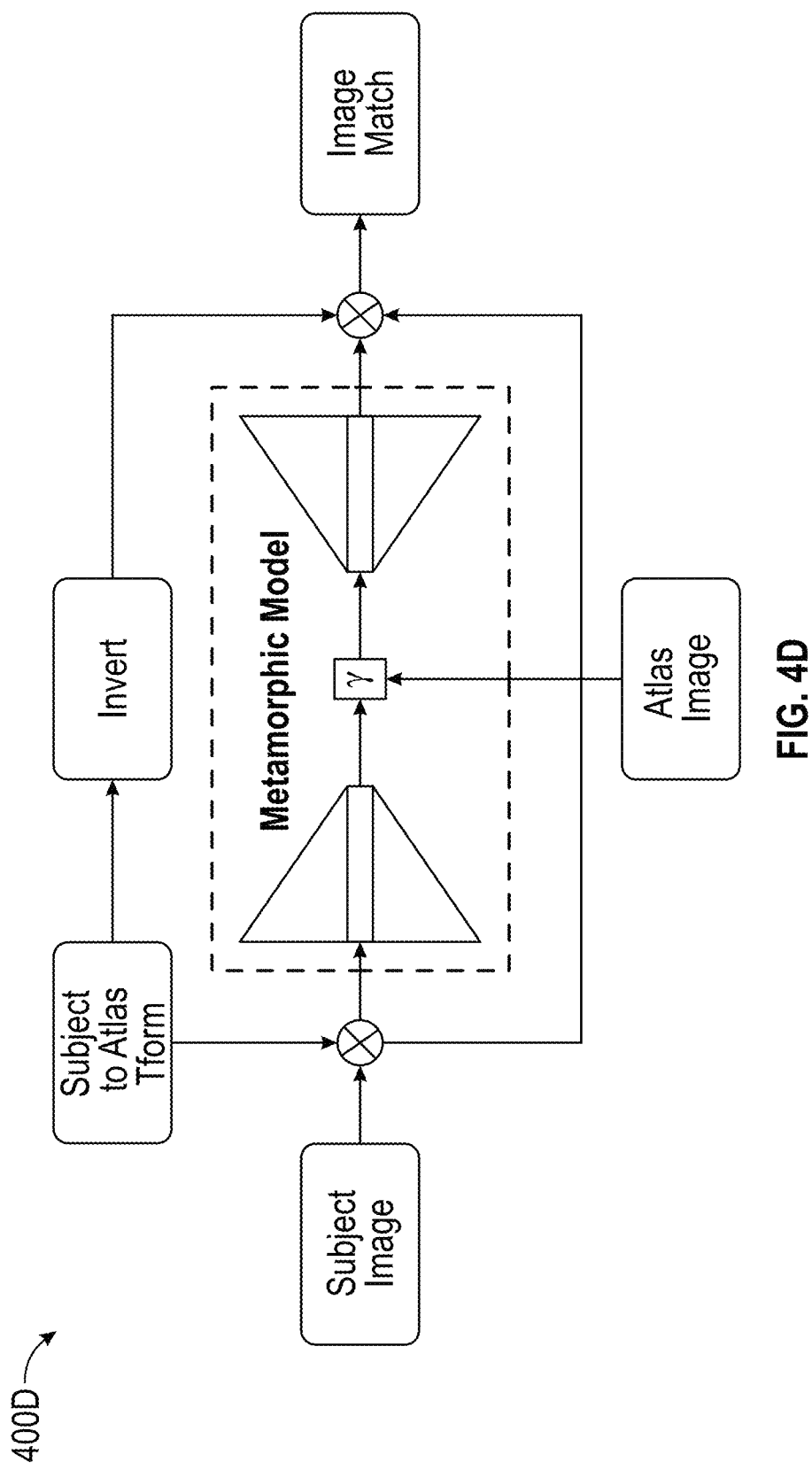
FIG. 4D depicts a flow diagram of a method of metamorphic model learning retrofit, in accordance with embodiments of the disclosure.

FIG. 4D depicts a flow diagram of a method 400D of metamorphic model learning retrofit, in accordance with embodiments of the disclosure. In one embodiment, method 400D describes the changes referenced above using an autoencoder framework that can be retrofitted into the previously described methods. In one embodiment, whenever a moving image/planning time image is available, the image can be metamorphosized using a model. In one embodiment, the metamorphic model may be constructed in a common atlas space. That is, the subject to atlas transformation may put the subject image into a common space where there exists correspondence between all the training images. The transformation model may be both optimized prior to the introduction of the metamorphic model and, when the models are refined, the objective function may include a term forcing the transformation model to explain as much variance as possible. Advantageously, this may ensure that changes that should be explained by a transformation model are not improperly explained by a metamorphic model. For example, a lack of alignment in two left femurs could be explained by either the disappearance of one femur and reappearance of a completely different femur or the rigid transformation of that femur.

FIG. 4D shows an autoencoder which takes in an image and outputs a different image. That image is then combined with the subject image and atlas image and then transformed to the target space. Many variants on this scheme are possible, a key being that the models should be applicable to the method 300A shown in FIG. 3A. A possible embodiment may ignore the subject image and generate the metamorphosed image as a modified version of the atlas image. In another embodiment, the metamorphic model may produce an image that is, after being appropriately transformed, added to the subject image.

In addition to the changes described above, which are intra-modality, a metamorphic method may be used to account for inter-modality changes. For example, the attenuation as measured by a 120 kVp x-ray beam may be different from that measured by a 150 kVp projection x-ray and may be different from a 6 MeV therapy beam. This method could be used to correct for such changes during registration and to correct for changes from kV imaging to MeV treatment/imaging beam, where dose calculation can be more accurate if a better attenuation map at the treatment energy is available. Furthermore, this can be extended to truly inter-modality cases, for example, CT to MR to x-ray. This is possible because the metamorphic model is constructed in an atlas coordinate system in which correspondence is available for all subjects.

In one embodiment, the models that are described herein are primarily intended to be used during a 3-D/2-D registration, but learning is performed in a 3-D/3-D context. In a 3-D/2-D problem, the imaging system may be more sensitive to certain changes than others in an imaging geometry dependent way. For example, with an x-ray image taken from the subject's anterior to posterior, more information about transformations in the superior-inferior direction and in the left-right direction is measured. In the primary imaging geometry, this x-ray imaging system rotates about the subject's superior-inferior axis, where each image has an axis of insensitivity that is always orthogonal to the superior-inferior axis.

Since the 3-D/2-D problem is underdetermined, the resolution described here relies on that fact that certain transformations are likely and, implicitly, that there are certain modes of transformations that occur together. For example, downward motion of the diaphragm is likely to be correlated with other changes associated with inspiration. As such, if the diaphragm is observed to move down, other transformations can be inferred. In one embodiment, these modes may be constructed with knowledge of how they are to be measured such that the modes can be constructed so that they can be optimally measured.

This can be accomplished by, when training models, optimizing over a function that, in addition to optimizing other terms, also includes a term forcing the modes to be visible under the imaging geometry. Such a term can be constructed as follows: when computing 3-D/3-D image matches, a DRR or set of DRRs should also be calculated using the desired imaging geometry. At treatment time there is a proposed 2-D image match term, for example, the sum of squared differences between the DRR and the measured x-ray. Parameters that produce modes that produce larger changes in the 2-D image match term with respect to a given change in transformation produce modes that are more visible under the proposed imaging geometry. This is described by the gradient of the image match term and the bigness of this value is the gradient magnitude. The measured image can be guessed if necessary. Another variant on this uses some metric of the Hessian matrix of the patient specific deformation model to perform a similar computation.

Figure 5:
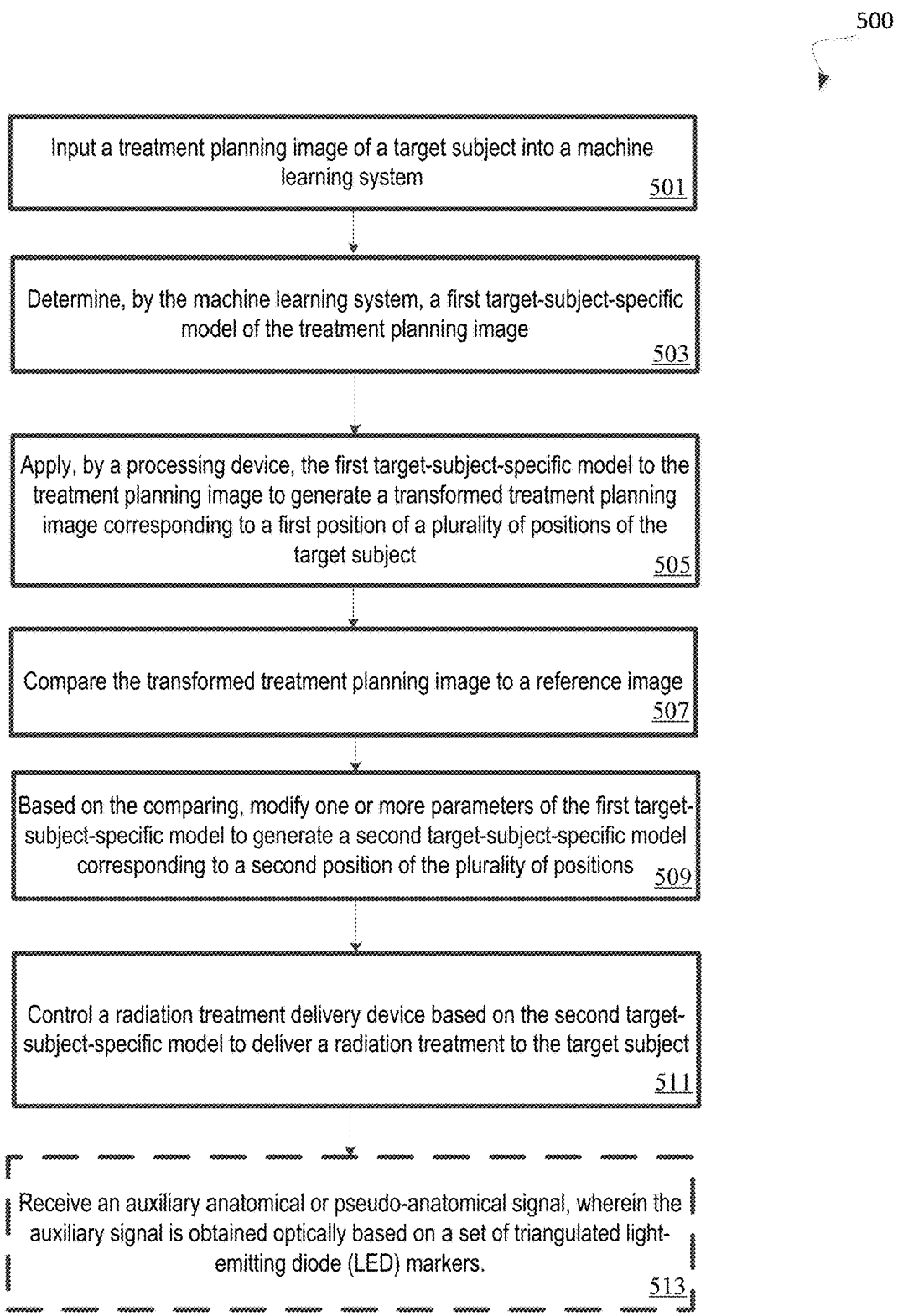
FIG. 5 depicts a flow diagram of a method of generating a partial deformation map for reconstructing motion-affected treatment dose using machine learning, in accordance with embodiments of the disclosure.

FIG. 5 depicts a flow diagram of a method 500 of generating a partial deformation map for reconstructing motion-affected treatment dose using machine learning, in accordance with embodiments of the disclosure. In general, each of the methods described herein (including method 500) may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the methods may be performed by processing logic of the radiation treatment system 800 of FIG. 1A.

Method 500 begins with processing logic at block 501 inputting a treatment planning image of a target subject into a machine learning system (e.g., using any of the machine learning models described or contemplated herein). In one embodiment, the treatment planning image is one of 3-D or 4-D anatomical images. In another embodiment, the transformed treatment planning image and the reference image are 2-D images.

At block 503, processing logic determines, by the machine learning system, a first target-subject-specific model of the treatment planning image. In one embodiment, the machine learning system is trained to construct the first target-subject-specific model from a 3-D, 4-D, or other derived image of the target subject. In another embodiment, the machine learning system is trained to construct the first target-subject-specific model from at least one deformable registration between the target subject and another subject. In yet another embodiment, the machine learning system is trained to construct the first target-subject-specific model from at least one deformable registration between the target subject at a first time and the target subject at a second time. In a further embodiment, the machine learning system is trained to construct the first target-subject-specific model from at least one deformable registration between the target subject and a synthesized atlas subject.

In one embodiment, the machine learning system uses a population of training subjects and a plurality of images associated with each of a plurality of training subjects as training data. In another embodiment, the machine learning system uses calculated subject-specific models as training data. In one embodiment, the subject-specific models comprise a central atlas of the target subject and a set of basis transformations and appearance changes that are combined linearly to produce an estimate of one or more conformations in which the target subject may be found.

In another embodiment, the subject-specific models comprise a model synthesis function comprising at least one of: linear combinations of basis functions or neural networks. In yet another embodiment, the subject-specific models may be developed from dimensionality reduction on a set of at least one of: real or synthetic data.

At block 505, processing logic applies (e.g., by a processing device) the first target-subject-specific model to the treatment planning image to generate a transformed treatment planning image corresponding to a first position of a plurality of positions of the target subject. At block 507, processing logic compares the transformed treatment planning image to a reference image.

At block 509, based on the comparing, processing logic modifies one or more parameters of the first target-subject-specific model to generate a second target-subject-specific model corresponding to a second position of the plurality of positions. At block 511, processing logic controls a treatment device based on the second target-subject-specific model to deliver a treatment to the target subject. Optionally, at block 513, processing logic may receive an auxiliary anatomical or pseudo-anatomical signal. In one embodiment, the auxiliary signal is obtained optically based on a set of triangulated light-emitting diode (LED) markers.

In one embodiment, the machine learning system uses a generative adversarial network that produces subject-specific models as its output. In another embodiment, the machine learning system uses an autoencoder network from which a decoder component can be used as the first subject-specific model. In a further embodiment, the machine learning system uses transfer learning from a system that produces subject-specific models from a subject to produce subject-specific models for another subject.

Figure 6:
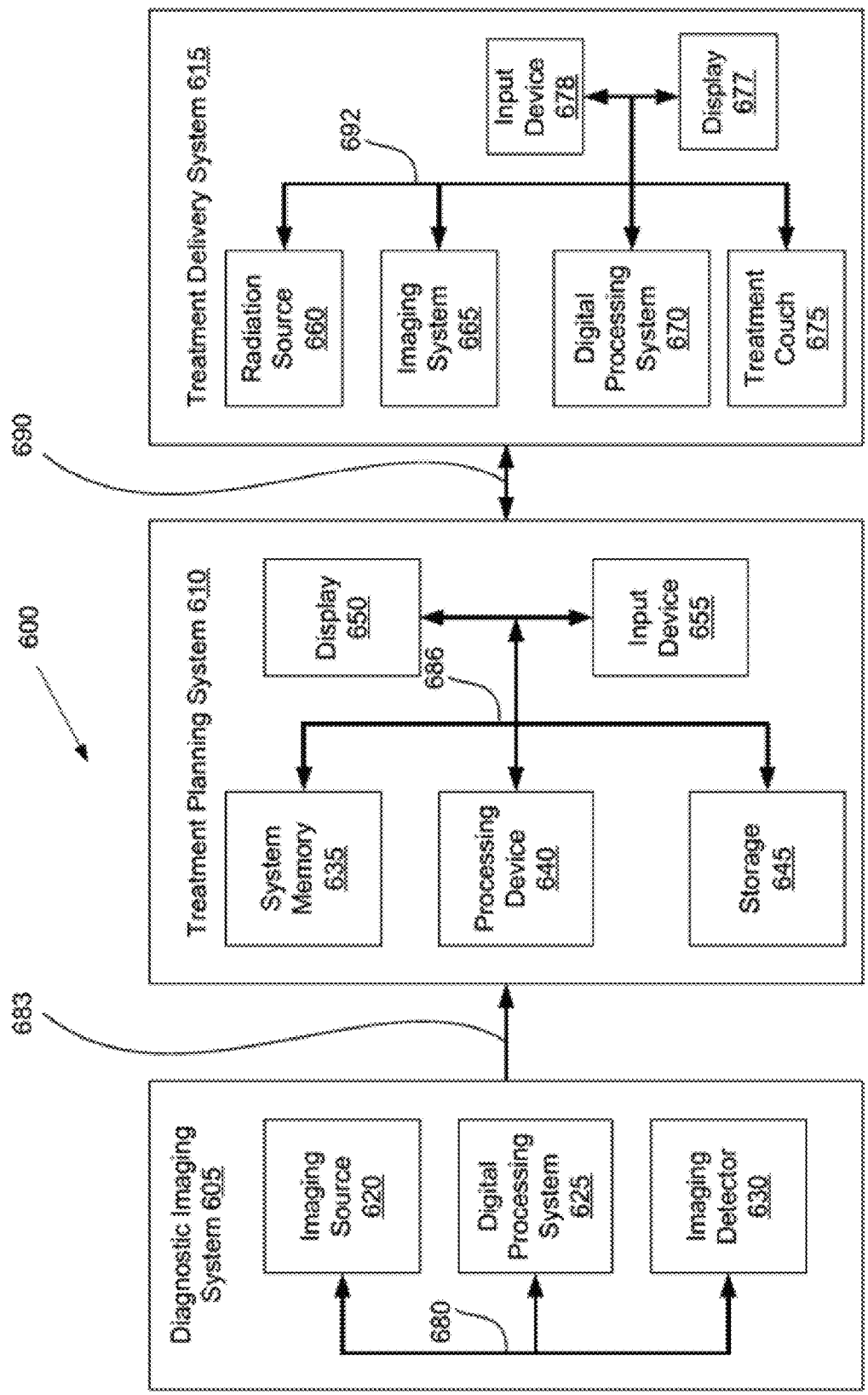
FIG. 6 illustrates examples of different systems that may be used to generate a partial deformation map for reconstructing motion-affected treatment dose, in accordance with embodiments described herein.

FIG. 6 illustrates examples of different systems 600 within which a set of instructions, for causing the systems to perform any one or more of the methodologies discussed herein, may be executed. In alternative implementations, the machine may be connected (e.g., networked) to other machines in a LAN, an intranet, an extranet, and/or the Internet. Each of the systems may operate in the capacity of a server or a client machine in client-server network environment, as a peer machine in a peer-to-peer (or distributed) network environment, or as a server or a client machine in a cloud computing infrastructure or environment.

The systems are machines capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

As described below and illustrated in FIG. 6, a system 600 may include a diagnostic imaging system 605, a treatment planning system 610, and a treatment delivery system 615. Diagnostic imaging system 605 may be any system capable of producing medical diagnostic images of a patient that may be used for subsequent medical diagnosis, treatment planning, treatment simulation and/or treatment delivery. For example, diagnostic imaging system 605 may be a computed tomography (CT) system, a magnetic resonance imaging (MRI) system, a positron emission tomography (PET) system, a combination of such systems, or the like. For ease of discussion, diagnostic imaging system 605 may be discussed below at times in relation to an x-ray imaging modality. In other embodiments, other imaging modalities such as those discussed above may also be used.

In one embodiment, diagnostic imaging system 605 includes an imaging source 620 to generate an imaging beam (e.g., x-rays) and an imaging detector 630 to detect and receive the beam generated by imaging source 620, or a secondary beam or emission stimulated by the beam from the imaging source (e.g., in an MM or PET scan).

In one embodiment, imaging source 620 and imaging detector 630 may be coupled to a digital processing system 625 to control the imaging operation and process image data. In one embodiment, diagnostic imaging system 605 may receive imaging commands from treatment delivery system 615 and/or treatment planning system 610.

Diagnostic imaging system 605 includes a bus or other means 680 for transferring data and commands among digital processing system 625, imaging source 620 and imaging detector 630. Digital processing system 625 may include one or more general-purpose processors (e.g., a microprocessor), special purpose processor such as a digital signal processor (DSP) or other type of processing device such as a controller or field programmable gate array (FPGA). Digital processing system 625 may also include other components (not shown) such as memory, storage devices, network adapters and the like. Digital processing system 625 may be configured to generate digital diagnostic images in a standard format, such as the Digital Imaging and Communications in Medicine (DICOM) format, for example.

In other embodiments, digital processing system 625 may generate other standard or non-standard digital image formats. Digital processing system 625 may transmit diagnostic image files (e.g., the aforementioned DICOM formatted files) to treatment delivery system 615 over a data link 683, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present disclosure to diagnose or treat a patient despite the existence of a physical separation between the system user and the patient.

In one embodiment, treatment delivery system 615 includes a therapeutic and/or surgical radiation source 660 to administer a prescribed radiation dose to a target volume in conformance with a treatment plan. Treatment delivery system 615 may also include imaging system 665 to perform computed tomography (CT) such as cone beam CT, and images generated by imaging system 665 may be two-dimensional (2-D) or three-dimensional (3-D).

Treatment delivery system 615 may also include a digital processing system 670 to control radiation source 660, receive and process data from diagnostic imaging system 605 and/or treatment planning system 610, and control a patient support device such as a treatment couch 675. Digital processing system 670 may be connected to or a part of a camera feedback system. Digital processing system 670 may be configured to perform any of the operations described herein. Digital processing system 670 may include a processing device that represents one or more general-purpose processors (e.g., a microprocessor), special purpose processor such as a digital signal processor (DSP) or other type of device such as a controller or field programmable gate array (FPGA). The processing device of digital processing system 670 may be configured to execute instructions to perform the operations described herein.

In one embodiment, digital processing system 670 includes system memory that may include a random access memory (RAM), or other dynamic storage devices, coupled to a processing device, for storing information and instructions to be executed by the processing device. The system memory also may be used for storing temporary variables or other intermediate information during execution of instructions by the processing device. The system memory may also include a read only memory (ROM) and/or other static storage device for storing static information and instructions for the processing device.

Digital processing system 670 may also include a storage device, representing one or more storage devices (e.g., a magnetic disk drive or optical disk drive) for storing information and instructions. The storage device may be used for storing instructions for performing the treatment delivery steps discussed herein. Digital processing system 670 may be coupled to radiation source 660 and treatment couch 675 by a bus 692 or other type of control and communication interface.

In one embodiment, the treatment delivery system 615 includes an input device 678 and a display 677 connected with digital processing system 670 via bus 692. The display 677 can show trend data that identifies a rate of target movement (e.g., a rate of movement of a target volume that is under treatment). The display can also show a current radiation exposure of a patient and a projected radiation exposure for the patient. The input device 678 can enable a clinician to adjust parameters of a treatment delivery plan during treatment.

Treatment planning system 610 includes a processing device 640 to generate and modify treatment plans and/or simulation plans. Processing device 640 may represent one or more general-purpose processors (e.g., a microprocessor), special purpose processor such as a digital signal processor (DSP) or other type of device such as a controller or field programmable gate array (FPGA). Processing device 640 may be configured to execute instructions for performing simulation generating operations and/or treatment planning operations discussed herein.

Treatment planning system 610 may also include system memory 635 that may include a random access memory (RAM), or other dynamic storage devices, coupled to processing device 640 by bus 686, for storing information and instructions to be executed by processing device 640. System memory 635 also may be used for storing temporary variables or other intermediate information during execution of instructions by processing device 640. System memory 635 may also include a read only memory (ROM) and/or other static storage device coupled to bus 686 for storing static information and instructions for processing device 640.

Treatment planning system 610 may also include storage device 645, representing one or more storage devices (e.g., a magnetic disk drive or optical disk drive) coupled to bus 686 for storing information and instructions. Storage device 645 may be used for storing instructions for performing the treatment planning steps discussed herein.

Processing device 640 may also be coupled to a display device 650, such as a cathode ray tube (CRT) or liquid crystal display (LCD), for displaying information (e.g., a 2-D or 3-D representation of the VOI) to the user. An input device 655, such as a keyboard, may be coupled to processing device 640 for communicating information and/or command selections to processing device 640. One or more other user input devices (e.g., a mouse, a trackball or cursor direction keys) may also be used to communicate directional information, to select commands for processing device 640 and to control cursor movements on display 650.

Treatment planning system 610 may share its database (e.g., data stored in storage 645) with a treatment delivery system, such as treatment delivery system 615, so that it may not be necessary to export from the treatment planning system prior to treatment delivery. Treatment planning system 610 may be linked to treatment delivery system 615 via a data link 690, which in one embodiment may be a direct link, a LAN link or a WAN link.

It should be noted that when data links 683, 686, and 690 are implemented as LAN or WAN connections, any of diagnostic imaging system 605, treatment planning system 610 and/or treatment delivery system 615 may be in decentralized locations such that the systems may be physically remote from each other. Alternatively, any of diagnostic imaging system 605, treatment planning system 610, and/or treatment delivery system 615 may be integrated with each other in one or more systems.

It will be apparent from the foregoing description that aspects of the present disclosure may be embodied, at least in part, in software. That is, the techniques may be carried out in a computer system or other data processing system in response to a processing device 625, 640, or 670 (see FIG.

6), for example, executing sequences of instructions contained in a memory. In various implementations, hardware circuitry may be used in combination with software instructions to implement the present disclosure. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by processing device 625, 640, or 670.

A machine-readable medium can be used to store software and data which when executed by a general purpose or special purpose data processing system causes the system to perform various methods of the present disclosure. This executable software and data may be stored in various places including, for example, system memory and storage or any other device that is capable of storing at least one of software programs or data. Thus, a machine-readable medium includes any mechanism that provides (i.e., stores) information in a form accessible by a machine (e.g., a computer, network device, personal digital assistant, manufacturing tool, any device with a set of one or more processors, etc.). For example, a machine-readable medium includes recordable/non-recordable media such as read only memory (ROM), random access memory (RAM), magnetic disk storage media, optical storage media, flash memory devices, etc. The machine-readable medium may be a non-transitory computer readable storage medium.

Unless stated otherwise as apparent from the foregoing discussion, it will be appreciated that terms such as "receiving," "positioning," "performing," "emitting," "causing," or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage or display devices. Implementations of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present disclosure are not described with reference to any particular programming language. It will be appreciated that a variety of programming languages may be used to implement implementations of the present disclosure.

It should be noted that the methods and apparatus described herein are not limited to use only with medical diagnostic imaging and treatment. In alternative implementations, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

In the foregoing specification, the disclosure has been described with reference to specific exemplary implementations thereof. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense.

What is claimed, is:

1. A method, comprising:
inputting a treatment planning image of a target subject into a machine learning system;
determining, by the machine learning system, a first target-subject-specific model of the treatment planning image;
applying, by a processing device, the first target-subject-specific model to the treatment planning image to generate a transformed treatment planning image corresponding to a first position of a plurality of positions of the target subject;
comparing the transformed treatment planning image to a reference image;
based on the comparing, modifying one or more parameters of the first target-subject-specific model to generate a second target-subject-specific model corresponding to a second position of the plurality of positions, wherein the first target-subject-specific model and the second target-subject-specific model each comprise a generative neural network to identify a reduced dimensionality of the treatment planning image and determining the transformed treatment planning image based on the reduced dimensionality; and
controlling a treatment device based on the second target-subject-specific model to deliver a treatment to the target subject.

2. The method of claim 1, wherein the treatment planning image is one of 3-D or 4-D anatomical images and wherein the transformed treatment planning image and the reference image are 2-D images.

3. The method of claim 1, wherein the machine learning system is trained to construct the first target-subject-specific model from a 3-D, 4-D, or other derived image of the target subject.

4. The method of claim 1, wherein the machine learning system is trained to construct the first target-subject-specific model from at least one deformable registration between the target subject and another subject.

5. The method of claim 1, wherein the machine learning system is trained to construct the first target-subject-specific model from at least one deformable registration between the target subject at a first time and the target subject at a second time.

6. The method of claim 1, wherein the machine learning system is trained to construct the first target-subject-specific model from at least one deformable registration between the target subject and a synthesized atlas subject.

7. The method of claim 1, wherein the machine learning system uses a population of training subjects and a plurality of images associated with each of a plurality of training subjects as training data.

8. The method of claim 1, wherein the machine learning system uses calculated subject-specific models as training data.

9. The method of claim 1, wherein the subject-specific models comprise a central atlas of the target subject and a set of basis transformations and appearance changes that are combined linearly to produce an estimate of one or more conformations in which the target subject may be found.

10. The method of claim 1, wherein the subject-specific models comprise a model synthesis function comprising at least one of: linear combinations of basis functions or neural networks.

11. The method of claim 1, wherein the subject-specific models are developed from dimensionality reduction on a set of at least one of: real or synthetic data.

12. The method of claim 1, wherein the machine learning system uses a generative adversarial network that produces subject-specific models as its output.

13. The method of claim 1, wherein the machine learning system uses an autoencoder network from which a decoder component can be used as the first subject-specific model.

14. The method of claim 1, wherein the machine learning system uses transfer learning from a system that produces subject-specific models from a subject to produce subject-specific models for another subject.

15. The method of claim 1, further comprising receiving an auxiliary anatomical or pseudo-anatomical signal.

16. A treatment system comprising:
a memory to store a treatment planning image of a target subject; and
a processing device, operatively coupled to the memory, the processing device to:
input the treatment planning image of the target subject into a machine learning system;
determine, by the machine learning system, a first target-subject-specific model of the treatment planning image;
apply the first target-subject-specific model to the treatment planning image to generate a transformed treatment planning image corresponding to a first position of a plurality of positions of the target subject;
compare the transformed treatment planning image to a reference image;
based on the comparing, modify one or more parameters of the first target-subject-specific model to generate a second target-subject-specific model corresponding to a second position of the plurality of positions, wherein the first target-subject-specific model and the second target-subject-specific model each comprise a generative neural network to identify a reduced dimensionality of the treatment planning image and determining the transformed treatment planning image based on the reduced dimensionality; and
control a treatment device based on the second target-subject-specific model to deliver a treatment to the target subject.

17. The treatment system of claim 16, wherein the treatment planning image is one of 3-D or 4-D anatomical images and wherein the transformed treatment planning image and the reference image are 2-D images.

18. The treatment system of claim 16, wherein the machine learning system is trained to construct the first target-subject-specific model from a 3-D, 4-D, or other derived image of the target subject.

19. The treatment system of claim 16, wherein the machine learning system is trained to construct the first target-subject-specific model from at least one deformable registration between the target subject and another subject.

20. The treatment system of claim 16, wherein the machine learning system is trained to construct the first target-subject-specific model from at least one deformable registration between the target subject at a first time and the target subject at a second time.

21. The treatment system of claim 16, wherein the machine learning system is trained to construct the first target-subject-specific model from at least one deformable registration between the target subject and a synthesized atlas subject.

22. The treatment system of claim 16, wherein the machine learning system uses a population of training subjects and a plurality of images associated with each of a plurality of training subjects as training data.

23. The treatment system of claim 16, wherein the machine learning system uses calculated subject-specific models as training data.

24. The treatment system of claim 16, wherein the subject-specific models comprise a central atlas of the target subject and a set of basis transformations and appearance changes that are combined linearly to produce an estimate of one or more conformations in which the target subject may be found.

25. The treatment system of claim 16, wherein the subject-specific models comprise a model synthesis function comprising at least one of: linear combinations of basis functions or neural networks.

26. The treatment system of claim 16, wherein the subject-specific models are developed from dimensionality reduction on a set of at least one of: real or synthetic data.

27. The treatment system of claim 16, wherein the machine learning system uses a generative adversarial network that produces subject-specific models as its output.

28. The treatment system of claim 16, wherein the machine learning system uses an autoencoder network from which a decoder component can be used as the first subject-specific model.

29. The treatment system of claim 16, wherein the machine learning system uses transfer learning from a system that produces subject-specific models from a subject to produce subject-specific models for another subject.

30. The treatment system of claim 16, the processing device further to receive an auxiliary anatomical or pseudo-anatomical signal, wherein the auxiliary signal is obtained optically based on a set of triangulated light-emitting diode (LED) markers.

31. The treatment system of claim 16, further comprising:
a gantry coupled to the radiation source, wherein the gantry is configured to rotate the radiation source about the target subject.

32. The treatment system of claim 31, wherein the gantry comprises a C-arm gantry.

33. The treatment system of claim 31, wherein the gantry comprises a ring gantry.

34. The treatment system of claim 16, further comprising:
a robotic arm coupled to the radiation source, wherein the robotic arm is configured to position the radiation source at a plurality of positions.

35. The treatment system of claim 34, wherein the robotic arm positions the radiation source at the plurality of positions about the target subject.

36. The treatment system of claim 16, wherein the radiation beam comprises a kilovolt (kV) treatment beam.

37. The treatment system of claim 16, further comprising a binary MLC.

38. A non-transitory, computer-readable storage medium comprising instructions, which when executed by a processing device, cause the processing device to:
input a treatment planning image of a target subject into a machine learning system;
determine, by the machine learning system, a first target-subject-specific model of the treatment planning image;

apply, by the processing device, the first target-subject-specific model to the treatment planning image to generate a transformed treatment planning image corresponding to a first position of a plurality of positions of the target subject;
compare the transformed treatment planning image to a reference image;
based on the comparing, modify one or more parameters of the first target-subject-specific model to generate a second target-subject-specific model corresponding to a second position of the plurality of positions, wherein the first target-subject-specific model and the second target-subject-specific model each comprise a generative neural network to identify a reduced dimensionality of the treatment planning image and determining the transformed treatment planning image based on the reduced dimensionality; and
control a treatment device based on the second target-subject-specific model to deliver a treatment to the target subject.

39. The non-transitory, computer-readable storage medium of claim 38, wherein the treatment planning image is one of 3-D or 4-D anatomical images and wherein the transformed treatment planning image and the reference image are 2-D images.

40. The non-transitory, computer-readable storage medium of claim 38, wherein the machine learning system is trained to construct the first target-subject-specific model from a 3-D, 4-D, or other derived image of the target subject.

41. The non-transitory, computer-readable storage medium of claim 38, wherein the machine learning system is trained to construct the first target-subject-specific model from at least one deformable registration between the target subject and another subject.

42. The non-transitory, computer-readable storage medium of claim 38, wherein the machine learning system is trained to construct the first target-subject-specific model from at least one deformable registration between the target subject at a first time and the target subject at a second time.

43. The non-transitory, computer-readable storage medium of claim 38, wherein the machine learning system is trained to construct the first target-subject-specific model from at least one deformable registration between the target subject and a synthesized atlas subject.

44. The non-transitory, computer-readable storage medium of claim 38, wherein the machine learning system uses a population of training subjects and a plurality of images associated with each of a plurality of training subjects as training data.

45. The non-transitory, computer-readable storage medium of claim 38, wherein the machine learning system uses calculated subject-specific models as training data.

46. The non-transitory, computer-readable storage medium of claim 38, wherein the subject-specific models comprise a central atlas of the target subject and a set of basis transformations and appearance changes that are combined linearly to produce an estimate of one or more conformations in which the target subject may be found.

47. The non-transitory, computer-readable storage medium of claim 38, wherein the subject-specific models comprise a model synthesis function comprising at least one of:
linear combinations of basis functions or neural networks.

48. The non-transitory, computer-readable storage medium of claim 38, wherein the subject-specific models are developed from dimensionality reduction on a set of at least one of: real or synthetic data.

49. The non-transitory, computer-readable storage medium of claim 38, wherein the machine learning system uses a generative adversarial network that produces subject-specific models as its output.

50. The non-transitory, computer-readable storage medium of claim 38, wherein the machine learning system uses an autoencoder network from which a decoder component can be used as the first subject-specific model.

51. The non-transitory, computer-readable storage medium of claim 38, wherein the machine learning system uses transfer learning from a system that produces subject-specific models from a subject to produce subject-specific models for another subject.

* * * * *